(12) United States Patent
Okihisa et al.

(10) Patent No.: US 8,162,893 B2
(45) Date of Patent: Apr. 24, 2012

(54) TROCAR STABILITY ASSEMBLY

(75) Inventors: David T. Okihisa, Irvine, CA (US);
Russell E. Ahlberg, Ranch Santa Margarita, CA (US); Gary M. Johnson, Mission Viejo, CA (US); Jeremy J. Albrecht, Ladera Ranch, CA (US); Michael L. Michaud, Lake Forest, CA (US); Benjamin A. Gianneschi, Orange, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 310 days.

(21) Appl. No.: 12/354,429

(22) Filed: Jan. 15, 2009

(65) Prior Publication Data
US 2009/0182282 A1 Jul. 16, 2009

Related U.S. Application Data

(60) Provisional application No. 61/021,214, filed on Jan. 15, 2008.

(51) Int. Cl.
*A61M 5/178* (2006.01)
(52) U.S. Cl. .................................. 604/165.01
(58) Field of Classification Search .................. 604/165
See application file for complete search history.

(56) References Cited

U.S. PATENT DOCUMENTS

| | | |
|---|---|---|
| 2,185,927 A | 1/1940 | Shelanski |
| 3,817,251 A | 6/1974 | Hasson |
| 4,617,933 A | 10/1986 | Hasson |
| 4,699,616 A | 10/1987 | Nowak et al. |
| 5,002,557 A | 3/1991 | Hasson |
| 5,137,520 A | 8/1992 | Maxson et al. |
| 5,147,316 A | 9/1992 | Castillenti |
| 5,176,697 A | 1/1993 | Hasson et al. |
| 5,215,531 A | 6/1993 | Maxson et al. |
| D338,270 S | 8/1993 | Stephens et al. |
| 5,257,973 A | 11/1993 | Villasuso |
| 5,263,939 A | 11/1993 | Wortrich |
| 5,267,968 A | 12/1993 | Russo |
| 5,403,336 A | 4/1995 | Kieturakis et al. |
| 5,653,718 A | 8/1997 | Yoon |

(Continued)

FOREIGN PATENT DOCUMENTS
JP 2003/061970 3/2003

OTHER PUBLICATIONS

Ethicon Endo-Surgery, Johnson-Johnson Company, Endopath Xcel product brochure, "Blunt Tip Trocar" copyright 2004.

*Primary Examiner* — Nicholas Lucchesi
*Assistant Examiner* — Jason Flick
(74) *Attorney, Agent, or Firm* — John F. Heal

(57) ABSTRACT

A stability assembly for a trocar cannula includes a conical stability member, a base, and a cannula retention member. The base has a passage defining an inner surface, and a constriction in the passage. The cannula retention member is rotatable within the passage, and advancement of the cannula retention member over the constriction reduces the inner diameter of the passage to restrain a cannula in the passage. Various latch mechanisms including interface surfaces on the base and the cannula retention member can be used in the stability assembly to secure the stability assembly around a cannula. Various conical stability members can be used in the stability assembly.

18 Claims, 42 Drawing Sheets

U.S. PATENT DOCUMENTS

| | | |
|---|---|---|
| 5,713,869 A | 2/1998 | Morejon |
| 5,792,112 A * | 8/1998 | Hart et al. ............ 604/164.01 |
| 5,830,232 A | 11/1998 | Hasson |
| 5,833,666 A | 11/1998 | Davis et al. |
| 6,423,036 B1 | 7/2002 | Van Huizen |
| 6,654,991 B2 | 12/2003 | Berry, Jr. |
| 6,723,088 B2 | 4/2004 | Gaskill, III et al. |
| 6,908,454 B2 | 6/2005 | McFarlane |
| D537,941 S | 3/2007 | Haberland et al. |
| 2004/0215209 A1 * | 10/2004 | Almond et al. ............ 606/108 |
| 2005/0038453 A1 | 2/2005 | Raulerson |
| 2006/0276818 A1 | 12/2006 | Buser et al. |
| 2006/0293702 A1 | 12/2006 | Buser et al. |
| 2007/0088277 A1 * | 4/2007 | McGinley et al. ....... 604/167.01 |
| 2007/0213675 A1 | 9/2007 | Albrecht et al. |
| 2007/0239108 A1 | 10/2007 | Albrecht et al. |

* cited by examiner

TROCAR STABILITY ASSEMBLY

CROSS REFERENCE TO RELATED APPLICATIONS

This application claims the benefit of U.S. Provisional Patent Application Ser. No. 61/021,214, entitled STABILITY CONE, filed on Jan. 15, 2008, which is hereby incorporated herein by reference in its entirety.

BACKGROUND OF THE INVENTION

1. Field of the Invention

The present application relates to trocars or surgical access ports and in particular to stability assemblies releasably attached to the cannula of a trocar system.

2. Description of the Related Art

A stability assembly can be used with a blunt tip trocar in a laparoscopic surgery utilizing the Hassan technique. The stability assembly can maintain the stability of the trocar cannula within an abdominal port during the laparoscopic procedure. Previous stability assemblies have included conical stability members and lock members coupled to the stability members. The lock members allowed the stability members to be selectively positioned and repositioned at a desired point along the trocar cannula.

Previous stability assemblies suffered from various shortcomings, however. For example, the lock mechanisms could be complex, increasing costs and difficulties of manufacturing and assembly. These complex lock mechanisms could also be difficult to be engaged by the user.

SUMMARY OF THE INVENTION

In various embodiments, stability assemblies are provided herein that overcome certain of the aforementioned shortcomings, and provide certain other advantages. For example, the stability assemblies described herein can comprise a locking mechanism that attaches securely at a desired location along the length of the cannula, while being simple to manufacture and operate. Certain embodiments of stability assembly include a stability member such as a stability cone that is configured to maintain a reliable seal with the trocar cannula and the entry incision in order to maintain pressure within the surgical site.

In certain embodiments, a stability assembly for a trocar system is provided herein that comprises a stability member, a base, and a cannula retention member. The stability member has a generally conical outer surface and a lumen extending through the stability member. The base is positioned at least partially within the lumen of the stability member. The base has an outer surface and an inner surface defined by a passage extending therethrough. The passage is adapted to receive a cannula therethrough. The inner surface of the base includes at least one constriction. The cannula retention member is positioned at least partially within the passage of the base and is rotatably coupled to the base. The cannula retention member is rotatable between a first position in which the passage of the base and the retention member define a first inner diameter, and a second position in which a portion of the retention member is advanced over the constriction such that the passage of the base and the retention member define a second inner diameter smaller than the first inner diameter.

In other embodiments, a stability assembly for a trocar system is provided herein that comprises a stability member, a base, and a retention member. The stability member is adapted to seal an entry port incision. The stability member has a lumen extending therethrough. The lumen defines a longitudinal axis of the stability assembly. The base is positioned at least partially within the lumen. The base has a passage extending along the longitudinal axis. The passage is adapted to receive a cannula therein. The retention member is positioned such that the retention member and the passage define an inner diameter of the stability assembly. The retention member is rotatable about the longitudinal axis between a first position wherein the stability assembly has a first inner diameter and a second position wherein the stability assembly has a second inner diameter smaller than the first inner diameter.

In other embodiments, a stability assembly for a trocar system is provided herein that comprises a stability member, a base, a retention member, and a latch mechanism. The stability member is adapted to seal an entry port incision and has a lumen extending therethrough. The base has an outer surface and an inner surface defined by a passage extending therethrough. The base is positioned such that the passage extends through at least a portion of the lumen. The retention member is rotatably coupled to the base. The retention member and the base define an inner diameter of the stability assembly. The retention member is rotatable between a first position wherein the stability assembly has a first inner diameter and a second position wherein the stability assembly has a second inner diameter smaller than the first inner diameter. The latch mechanism is configured to selectively maintain the retention member in the second position.

In other embodiments, a stability assembly for a trocar system is provided herein that comprises a stability member, a base, and an actuator. The stability member is adapted to seal an entry port incision. The stability member has a lumen extending therethrough configured to receive a cannula. The base is positioned about a portion of the stability member. The base has a retention loop integrally formed therewith defining an inner diameter of the base. The retention loop partially surrounds the portion of the stability member. The actuator is coupled to the base and configured to actuate the retention loop. The actuator is movable between a first position in which the inner diameter has a first diameter and a second position in which the inner diameter has a second diameter smaller than the first diameter.

In other embodiments, a stability assembly for a trocar system is provided herein that comprises a stability member and a retention assembly. The stability member is adapted to seal an entry port incision. The stability assembly has a lumen extending therethrough configured to receive a cannula. The retention assembly comprises a base, a retention loop, and an actuator. The base is positioned about a portion of the stability member. The base has a passage therethrough for receiving a portion of the stability member. The base has a slot formed through a portion thereof extending between an outer surface of the base and the passage. The retention loop has a first portion extending around a portion of the base and a second portion extending through the slot of the base such that an inner diameter of the retention assembly is defined by an inner surface of the passage of the base and the second portion of the retention loop. The actuator is coupled to the retention loop and configured to actuate the retention loop. The actuator is movable between a first position in which the retention assembly has a first diameter and a second position in which the retention loop has a second diameter smaller than the first diameter.

DETAILED DESCRIPTION OF THE INVENTION

Figure 1:
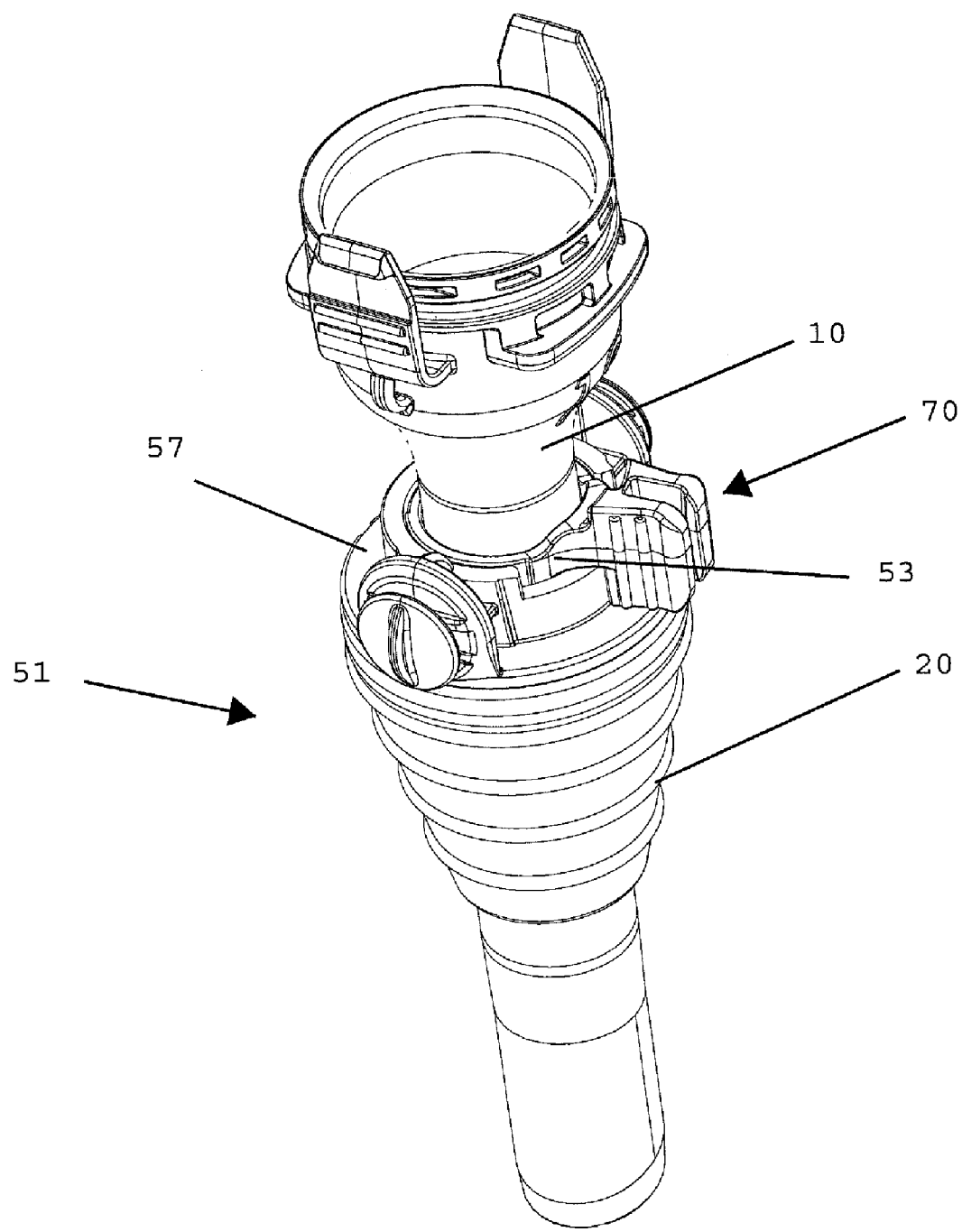
FIG. 1 is a perspective view of an embodiment of trocar assembly with stability assembly.
Figure 2:
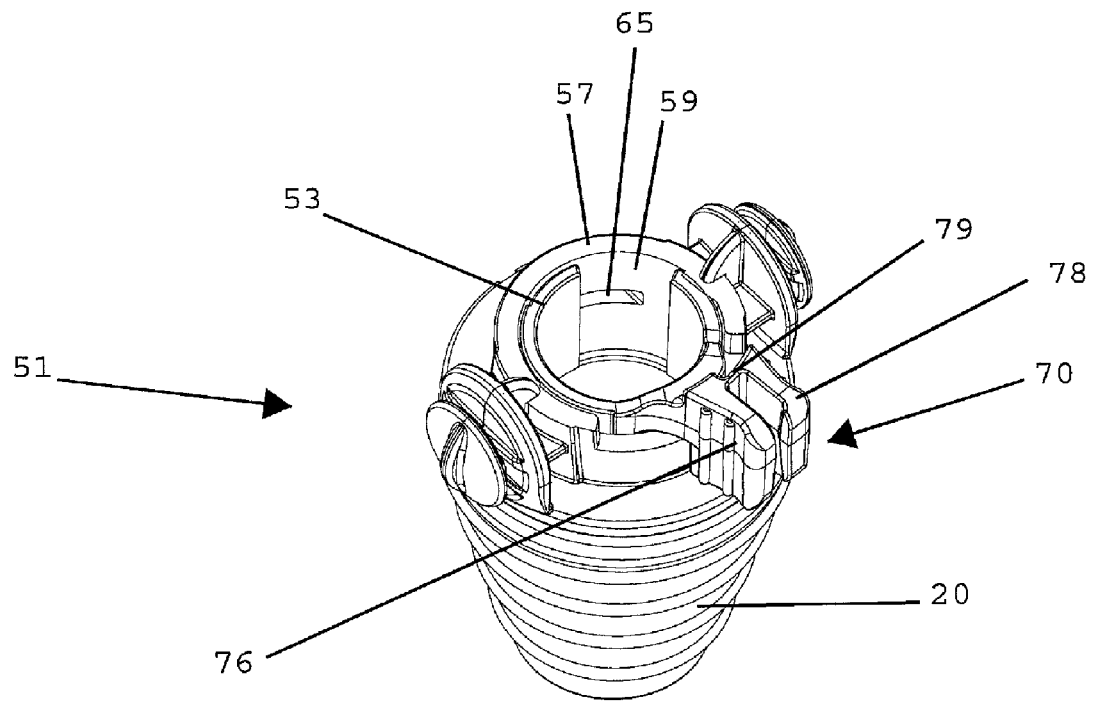
FIG. 2 is a perspective view of the stability assembly illustrated in FIG. 1.
Figure 3:
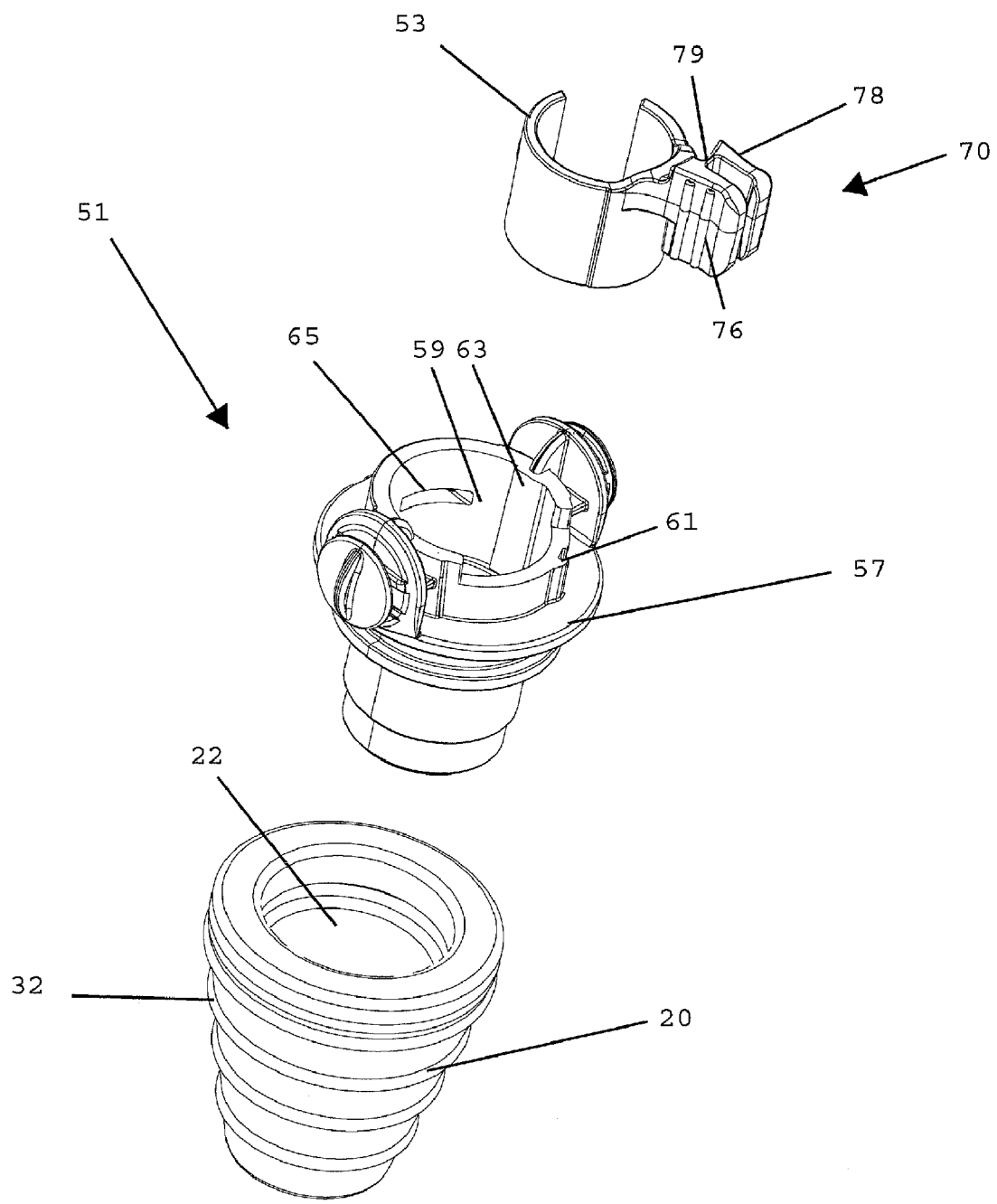
FIG. 3 is an exploded perspective view of the stability assembly illustrated in FIG. 1.
Figure 4A:
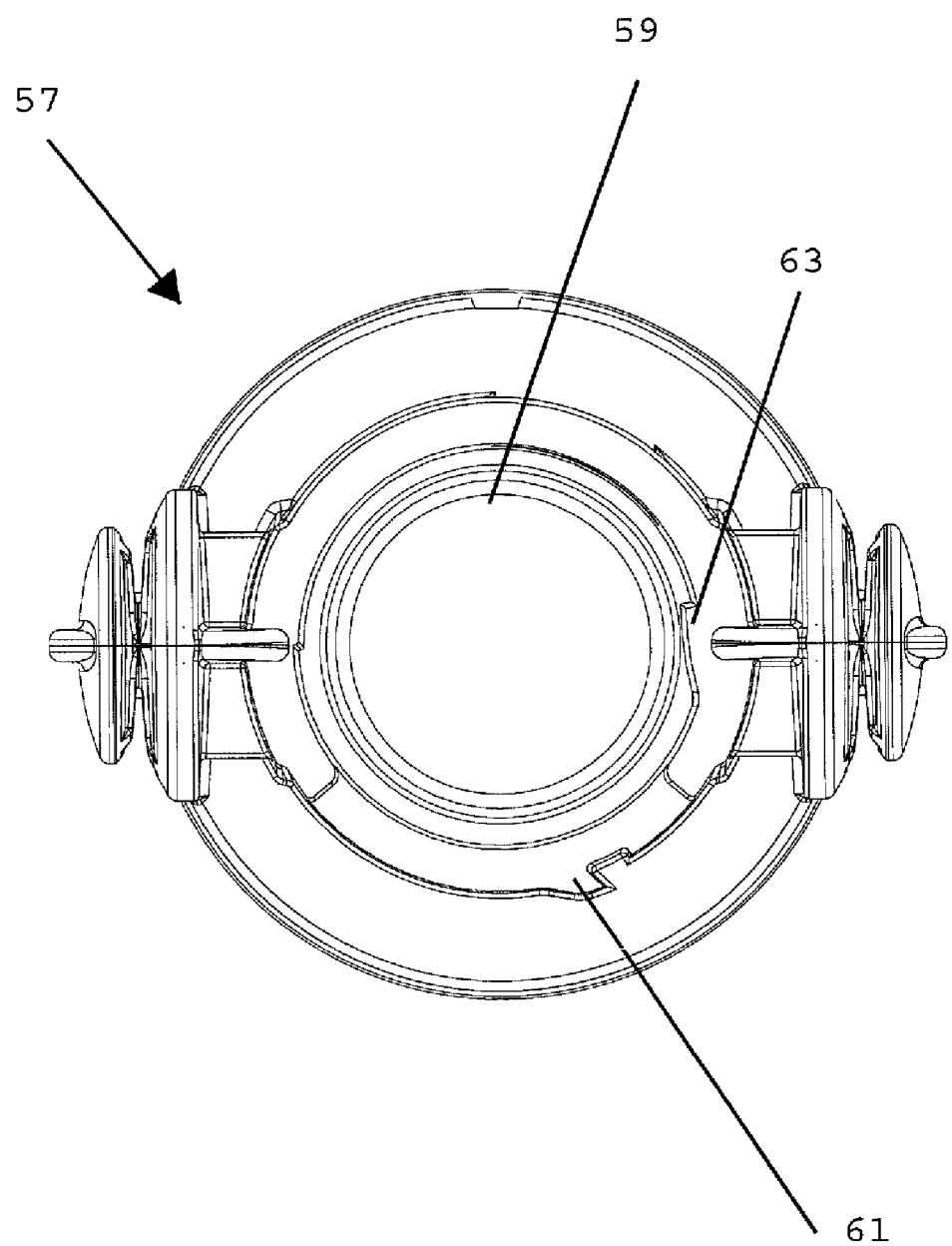
FIG. 4A is a top view of a base of the stability assembly illustrated in FIG. 1.
Figure 4B:
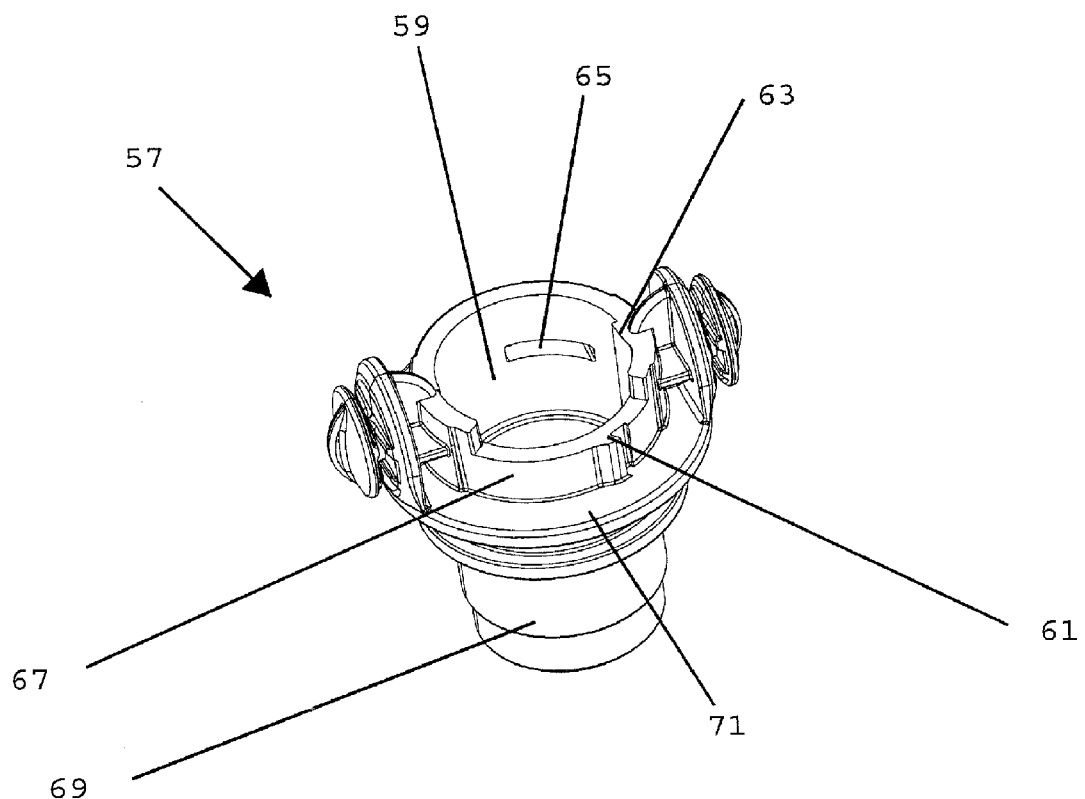
FIG. 4B is a perspective view of the base of the stability assembly illustrated in FIG. 1.

With reference to FIGS. 1-6, an embodiment of stability assembly for a trocar cannula is illustrated. In the illustrated embodiment, the stability assembly 51 comprises a stability member 20, cannula retention member 53, and a base 57. FIG. 1 illustrates a perspective view of the stability assembly 51 having a cannula 10 inserted longitudinally into the stability assembly 51 along a central longitudinal axis of the stability assembly 51. FIG. 2 illustrates a perspective view of the stability assembly 51 with a cannula 10 removed, and FIG. 3 illustrates an exploded perspective view of the stability assembly 51 with the cannula 10 removed.

Stability Member

With continued reference to FIGS. 1-6, the stability member 20 can have a generally conical outer surface extending from a relatively wide proximal end to relatively narrow distal end. As further described with respect to FIGS. 23 and 24, the stability member 20 can include a contoured outer surface including one or more protruding annular rings 32 (FIG. 3), a ramped surface, or another retention surface to enhance sealing and securing of the stability member 20 with an entry incision or access site.

In some embodiments, the stability member 20 can comprise a flexible material such as a silicone rubber. Advantageously, the flexibility of the stability member 20 can allow it to conform to an incision wall or uneven surrounding tissue while reducing the force applied and thereby minimizing potential trauma to tissue.

With reference to FIG. 3, the stability member 20 comprises a lumen 22 extending therethrough. The lumen 22 extends along the central longitudinal axis of the stability assembly from a proximal end to a distal end of the stability member 20. The lumen can be configured to receive at least a portion of the base 57 therein.

Base

With reference to FIGS. 1-6, in the illustrated embodiment, the base 57 comprises a generally cylindrical member having a proximal portion 67 and a distal portion 69. (FIG. 4B). An embodiment of the base 57 is illustrated in FIGS. 4A and 4B. FIG. 4A illustrates a top view of the base 57, and FIG. 4B illustrates a perspective view of the base 57. In the illustrated embodiment, the proximal portion 67 is adapted to receive the cannula retention member 53. As illustrated, the distal portion 69 is at least partially positioned within the lumen 22 of the stability member 20. (FIG. 3). The base 57 can also include at least one cylindrical flange 71 protruding therefrom.

In certain embodiments, the base 57 has an inner surface defined by a passage 59 extending therethrough along the longitudinal axis of the stability assembly. In certain embodiments, the base 57 is configured to couple with the cannula retention member 53 to selectively retain a cannula 10 (FIG. 1) positioned through the passage. The base 57 can include a diametric constriction, such as an inner ramped surface 63 or a region of increased wall thickness, formed in the passage 59 to cooperate with the cannula retention member 53 as further described herein. In certain embodiments, the base 57 can include a mating surface, such as an outer ramped surface 61 formed on the proximal portion 67 of the base 53 to cooperate with the cannula retention member as further described herein. In a certain embodiments, the base 57 can include a retention slot 65, formed through the proximal portion 67 of the base 57 to cooperate with the cannula retention member 53 as further described herein.

In certain embodiments, the base 57 can be formed by a molding operation. For example, in some embodiments, the base can be formed of an injection-molded thermoplastic material. Advantageously, this molded base can be durable and can be manufactured quickly and relatively inexpensively.

Cannula Retention Member

With continued reference to FIGS. 1-6, in the illustrated embodiment, the cannula retention member 53 comprises an annular loop portion 72 and a lever portion 70. (FIGS. 5A, 5B). An embodiment of the cannula retention member 53 is illustrated in FIGS. 5A and 5B. FIG. 5A illustrates a top view of the cannula retention member 53, and FIG. 5B illustrates a perspective view of the cannula retention member 53.

Figure 5A:
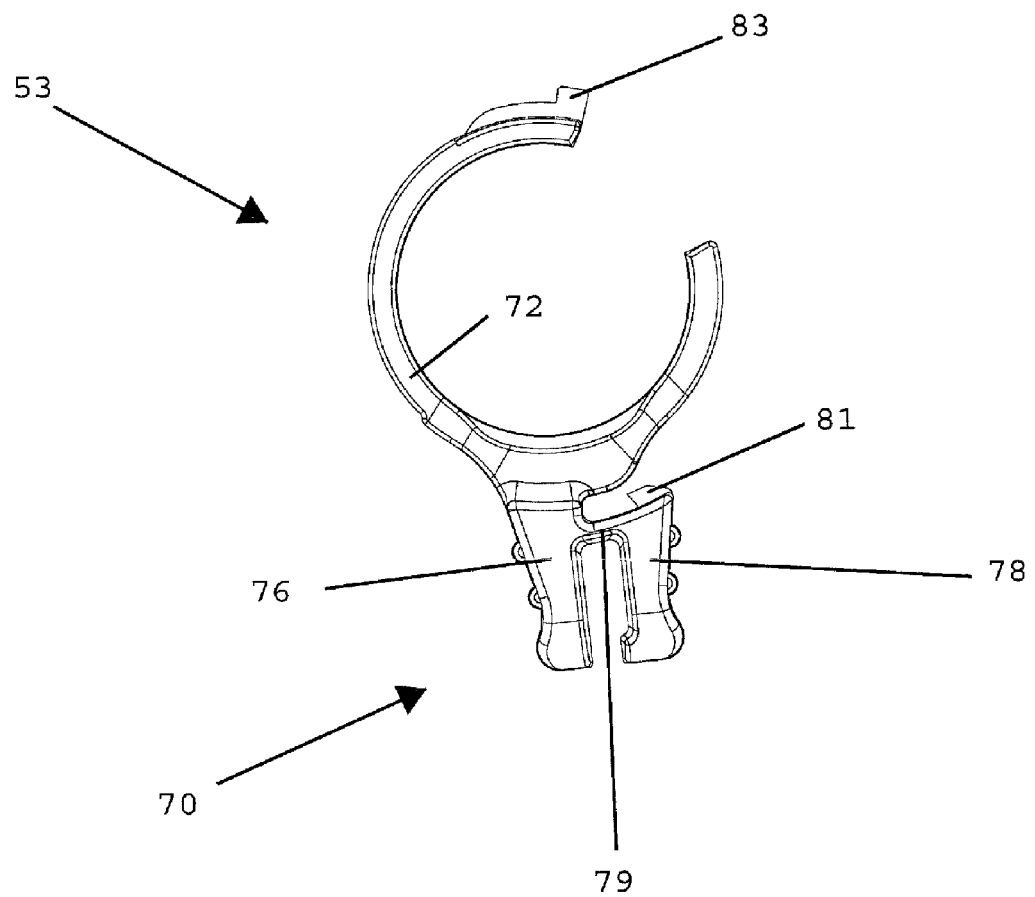
FIG. 5A is a top view of a cannula retention member of the stability assembly illustrated in FIG. 1.
Figure 5B:
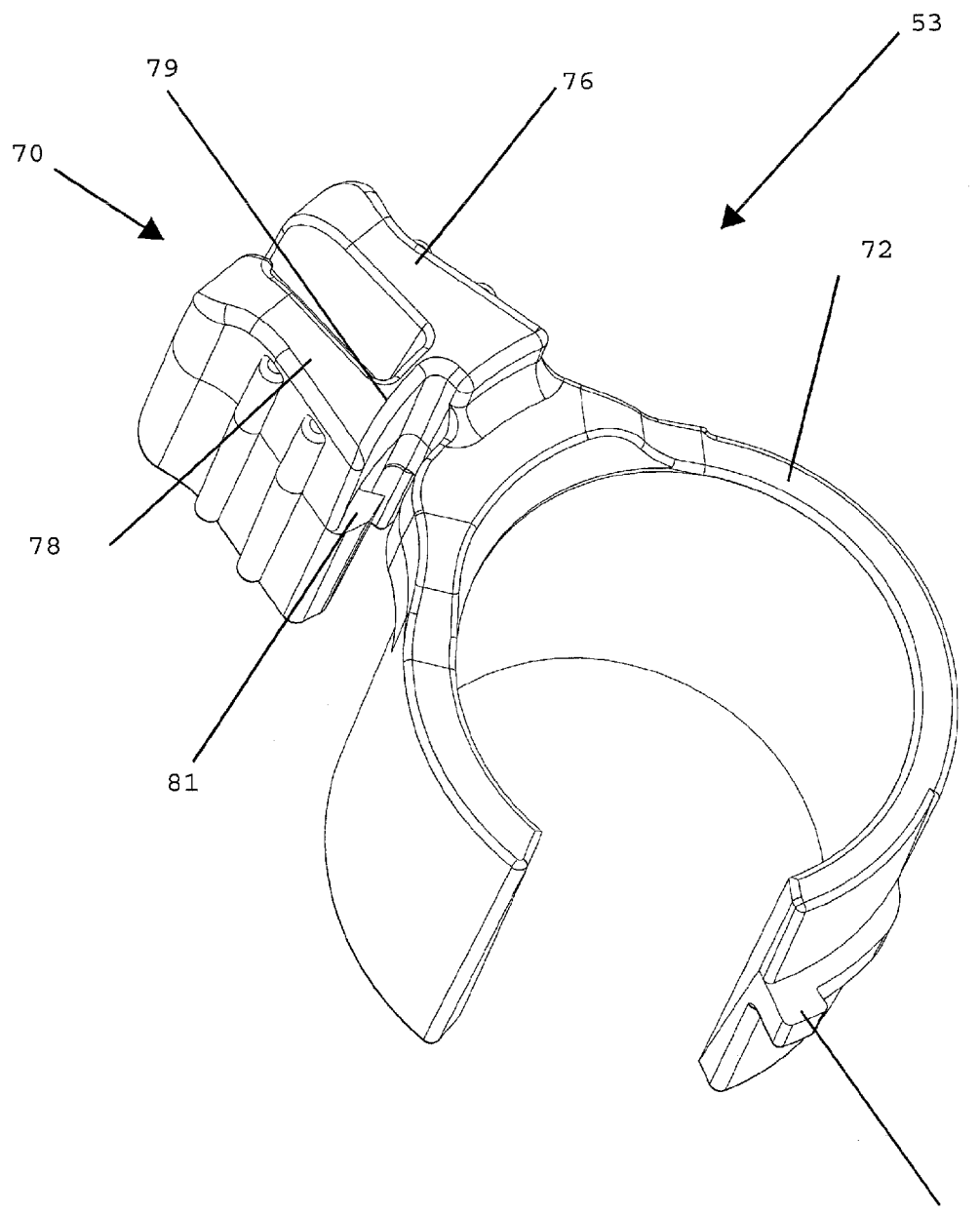
FIG. 5B is a perspective view of the cannula retention member of the stability assembly illustrated in FIG. 1.

With reference to FIGS. 5A and 5B, as illustrated, the annular loop portion 72 of the cannula retention member 53 comprises a generally cylindrical segment. Although in the illustrated embodiment, the annular loop portion 72 comprises a cylindrical segment spanning more than 270°, it is contemplated that in some embodiments, then annular loop portion can comprise a relatively small, less than approximately 180° cylindrical segment, an intermediate sized or "C-shaped" cylindrical segment, or a substantially cylindrical segment.

With continued reference to FIGS. 5A and 5B, desirably, the annular loop portion 72 of the cannula retention member is relatively flexible to cooperate with the base 57 as further described herein. In the illustrated embodiment, the annular loop portion 72 comprises a flexible material having a substantially constant wall thickness. However, it is contemplated that in other embodiments, wall thickness of the annular loop portion 72 could vary wall thickness, with locations of relatively thin wall thickness forming flexure regions of the loop portion.

With continued reference to FIGS. 5A and 5B, as illustrated, the annular loop portion 72 can comprise a retention tab 83 formed thereon. The retention tab 83 can extend from an outer surface of the annular loop portion 72, and can be sized and configured to fit within the retention slot 65 of the base 57. Advantageously, with the retention tab 83 positioned within the retention slot 65, longitudinal movement of the retention member 53 relative to the base 57 along the central longitudinal axis of the stability assembly can be restrained. Furthermore, the length of the retention slot 65 in the base 57 can define a range of rotational movement of the retention member 53 relative to the base 57 about the central longitudinal axis.

While the illustrated embodiments include a single retention tab 83 interfacing with a single retention slot 65, it is contemplated that in some embodiments, the retention member 53 can comprise a plurality of retention tabs, and the base 57 can comprise a corresponding plurality of retention slots. Furthermore, while the base 57 of the illustrated embodiment includes a retention slot 65 extending therethrough, it is contemplated that in other embodiments, a retention slot could be a groove or recess extending partially through the base 57.

With continued reference to FIGS. 5A and 5B, as illustrated, the lever portion 70 comprises an actuation lever 76, a latch lever 78, a flexible rib 79, and a latch tab 81. In the illustrated embodiment, an interface surface such as a latch tab 81 is formed at an end of the latch lever 78. As illustrated, the flexible rib 79 extends between the actuation lever 76 and the latch lever 78, and allows the latch lever 78 to be pivoted with respect to the actuation lever 76. This pivoting motion can move the latch tab 81 from a position relatively close to the annular loop portion 72 to a position spaced apart from the annular loop portion 72.

As illustrated, the actuation lever 76 and the latch lever 78 can have ribbed surfaces to enhance the grippability of the levers. In other embodiments, one or both of the levers 76, 78 can include texturing, contouring, or other surface features to enhance grippability.

In certain embodiments, the retention member 53 can be formed by a molding operation. For example, in some embodiments, the retention member 53 can be formed of an injection-molded thermoplastic material. Advantageously, this molded retention member can be manufactured quickly and relatively inexpensively. In some embodiments, both the base 57 and the retention member 53 are molded, and this commonality can lead to further manufacturing efficiencies and cost savings.

Operation

Figure 6A:
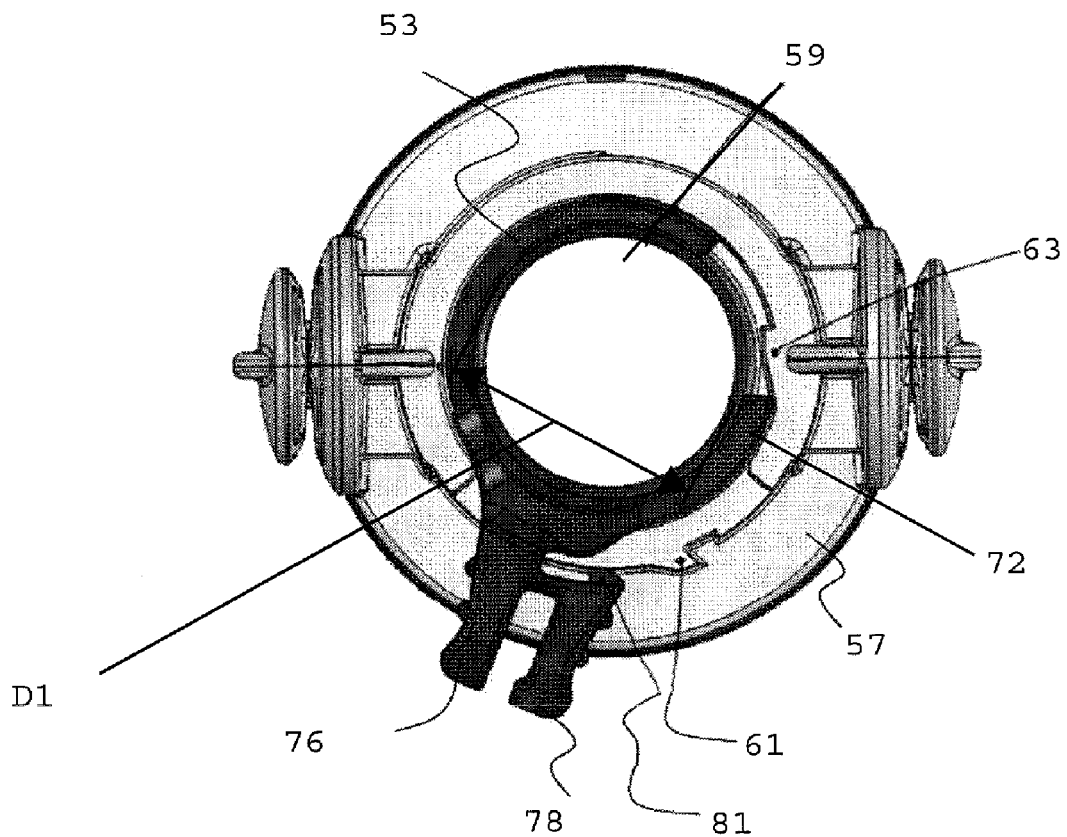
FIG. 6A is a top view of the base and cannula retention member of the stability assembly illustrated in FIG. 1 in a first position.
Figure 6B:
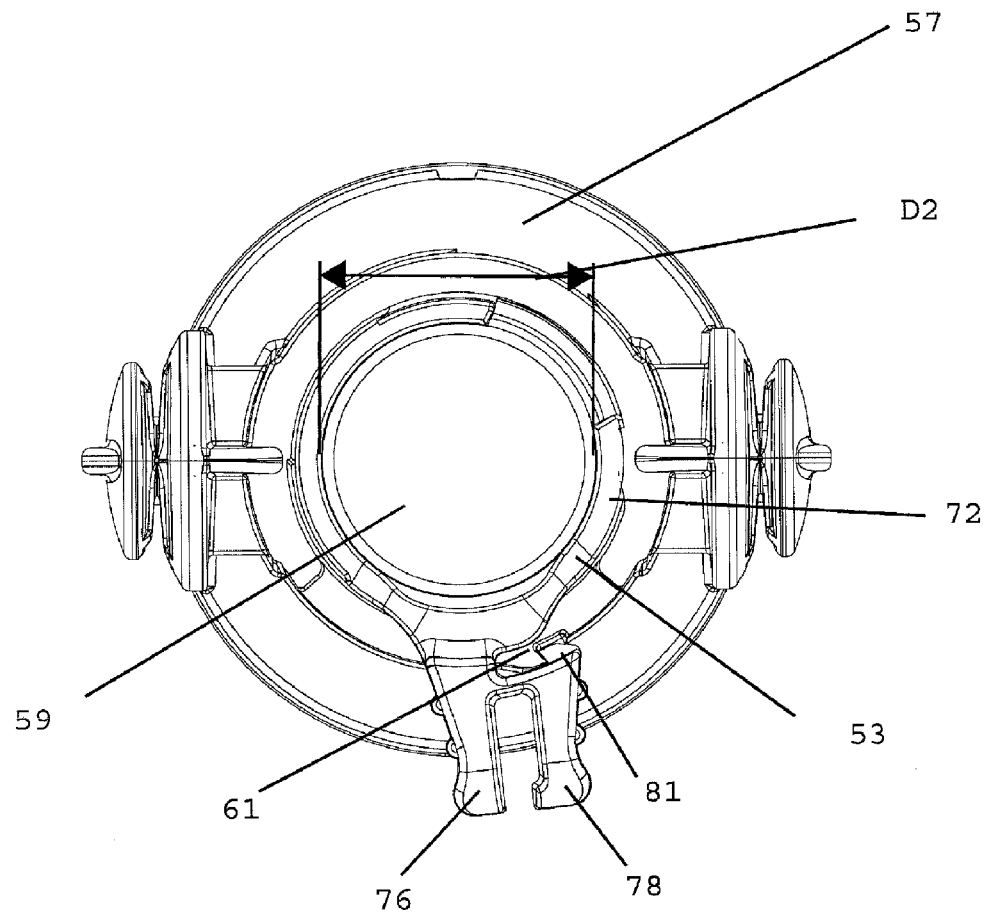
FIG. 6B is a top view of the base and cannula retention member of the stability assembly illustrated in FIG. 1 in a second position.

With reference to FIGS. 6A-6B, operation of the stability assembly 51 of FIGS. 1-6 is illustrated. FIG. 6A illustrates a top view of the stability assembly, with the retention member 53 rotated to a first position with respect to the base 57. FIG. 6B illustrates a top view of the stability assembly with the retention member 53 rotated to a second position with respect to the base 57.

With reference to FIG. 6A, with the retention member 53 in the first position, the annular loop portion 72 does not extend over substantially all of the ramped surface 63 formed in the passage 59 of the base 57. The passage 59 and the retention member 53 define an inner diameter of the stability assembly. As illustrated, with the retention member 53 in the first position, the stability assembly has a first diameter D1. Desirably, the base 57 and the retention member 53 can be sized and configured such that the first diameter D1 is larger than the outer diameter of a trocar cannula to be inserted into the stability assembly. For example, in some embodiments, the base 57 and cannula retention member 53 can be sized to allow the passage of a 12 mm cannula when the retention member 53 is in the first position. In other embodiments, the base 57 and cannula retention member 53 can be sized and configured to admit cannulae having other standard or non-standard sizes. Thus, with the retention member 53 in the first position, a trocar cannula 10 (FIG. 1) can be inserted into the passage 59 and moved until the stability assembly is at a desired location on the cannula 10.

With reference to FIG. 6B, with the retention member 53 in the second position, the annular loop portion 72 extends over at least a portion of the ramped surface 63 formed in the passage 59 of the base 57. With the retention member 53 in the second position, the stability assembly has a second diameter D2. During rotation of the retention member 53 from the first position to the second position, the annular loop portion 72 has been advanced over a portion of the ramped surface 63 of the base 57. In the second position, the ramped surface 63 directs the annular loop portion 72 into the passage, thus reducing the inner diameter of the stability assembly. Accordingly, the second diameter D2 of the stability assembly is smaller than the first inner diameter D1 of the stability assembly. Desirably, the base 57 and the retention member 53 can be sized and configured such that the second diameter D2 is smaller than the outer diameter of a trocar cannula to be inserted into the stability assembly. Accordingly, with the retention member 53 in the second position, the stability assembly 51 can apply a clamping force on an outer surface of the cannula 10. Thus, with the retention member 53 in the second position, the position of a trocar cannula 10 (FIG. 1) with respect to the stability member can be restrained with respect to the central longitudinal axis of the stability assembly.

To secure a cannula 10 in the stability assembly 51, a user can rotate the retention member 53 from the first position to the second position. The user can position a thumb or finger on the actuation lever 76 and advance the actuation lever 76 counterclockwise with respect to the central longitudinal axis of the illustrated embodiment of stability assembly. In other embodiments, the stability assembly can be configured such that clockwise advancement of the actuation lever advances the retention member 53 to the second position to restrain a cannula 10. With reference to FIGS. 6A and 6B, as the retention member 53 is advanced into the second position, the latch tab 81 is advanced over the outer ramped surface 61 of the base 57. This advancement of the latch tab 81 over the ramped surface 61 can move an inner surface of the annular loop portion 72 into the passage 59 of the base 57, which can cooperate to reduce the second diameter D2 of the stability assembly. Desirably, the ramped surface 61 and the latch tab 81 can be shaped and configured to interface as a latch mechanism when the retention member 53 is in the second position, forming a latched connection. For example, the outer ramped surface of the base 57 can include a ramp portion and a detent portion positioned such that the latch tab 81 is retained in the detent portion when retention member 53 is in the second position.

To release a cannula 10 from the stability assembly 51, either to reposition or remove the stability assembly from the cannula, a user can rotate the retention member 53 from the second position to the first position. To release the latched connection between the latch tab 81 and the outer ramped surface 61 of the base 57, the user can pivot the latch lever 78 with respect to the actuation lever 76, such as by squeezing the latch lover 78 and the actuation lever 76 with a thumb and finger. This pivot motion can disengage the latch tab 81 from the detent of the ramped surface 61 such that the retention member 53 can be freely rotated towards the first position with respect to the base 57.

Thus, in the illustrated embodiment, the latch tab 81 on the cannula retention member 53 and the outer ramped surface 61 on an outer surface of the base 57 form a latch mechanism that allows a user to selectively maintain the cannula retention member 53 in the second position. Advantageously, the latch mechanism is intuitive and easy to operate by a user. In certain commercial embodiments, the latch mechanism can be actively engaged by the user and as such in the initial or rest stage a stability assembly is not secured or latched to the outer surface of the cannula. Thus, if the cannula and stability assembly are packaged in an assembled state, i.e., cannula inserted through the stability assembly, the latch mechanism is less prone to failure due to stresses that may be induced on the stability assembly during storage. As such, packaging can be simplified or reduced as the stability assembly and cannula can be provided in the assembled state.

Stability Assemblies Having Various Latch Mechanisms

Figure 13:
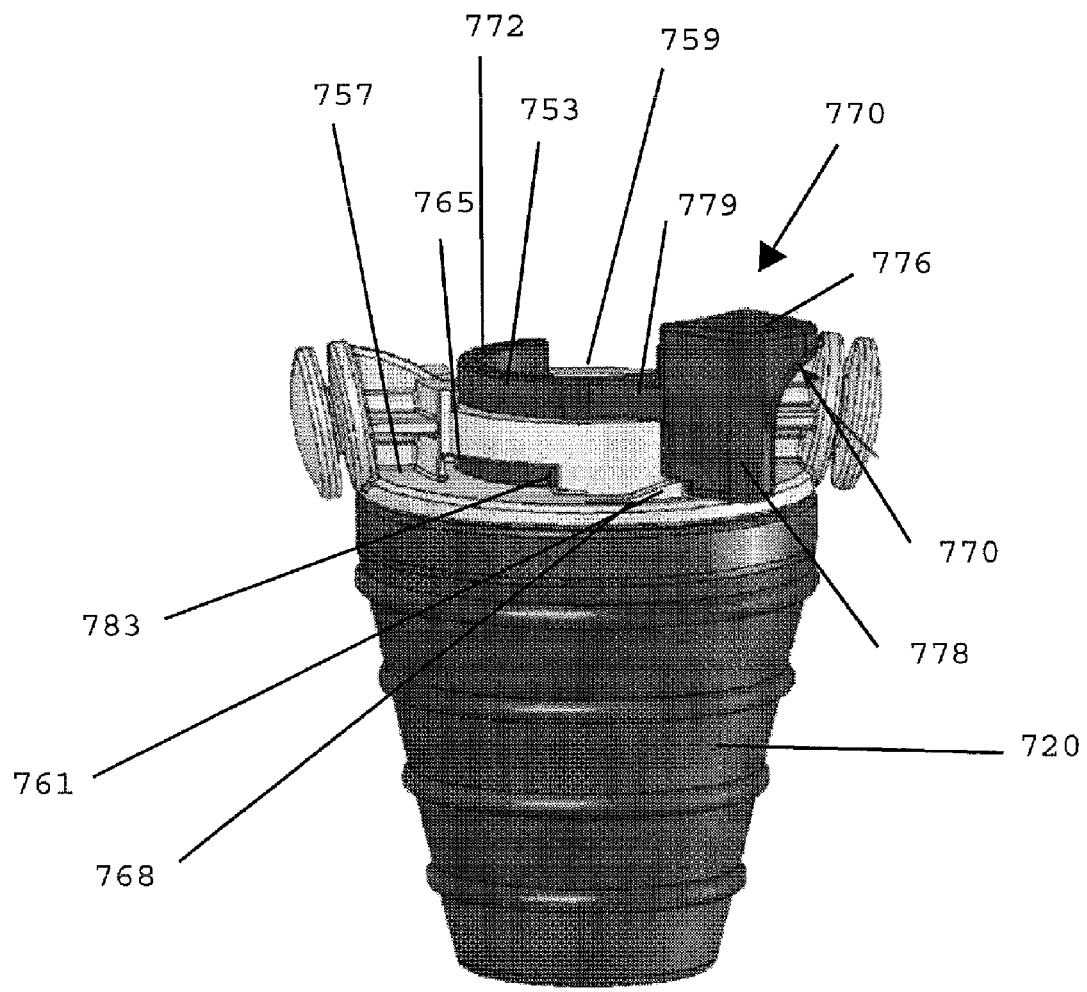
FIG. 13 is a perspective view of an embodiment of stability assembly.
Figure 14:
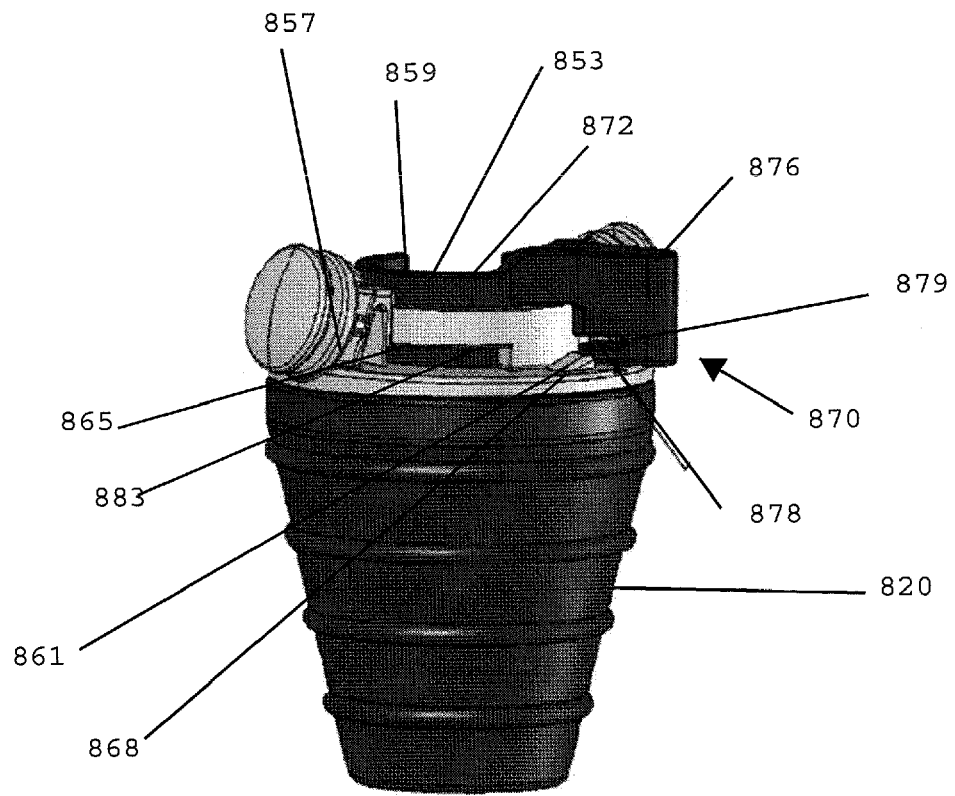
FIG. 14 is a perspective view of an embodiment of stability assembly.
Figure 15:
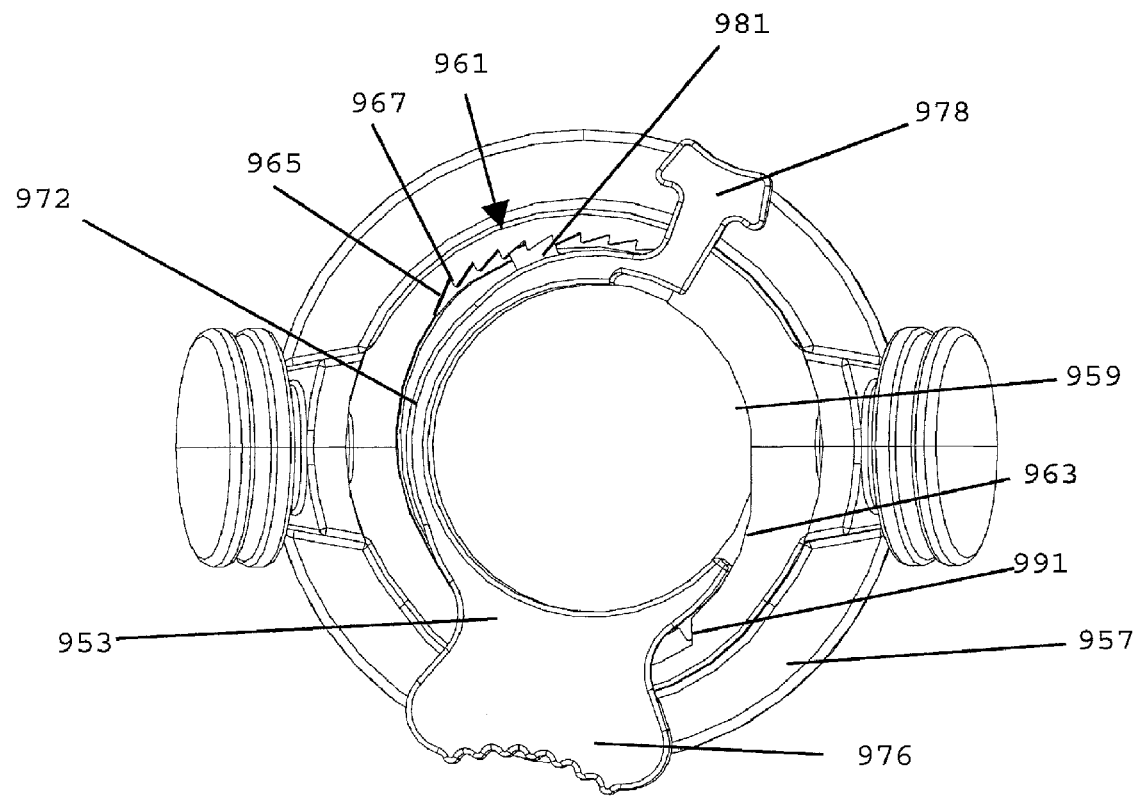
FIG. 15 is a top view of a base and cannula retention member of another embodiment of stability assembly.
Figure 16:
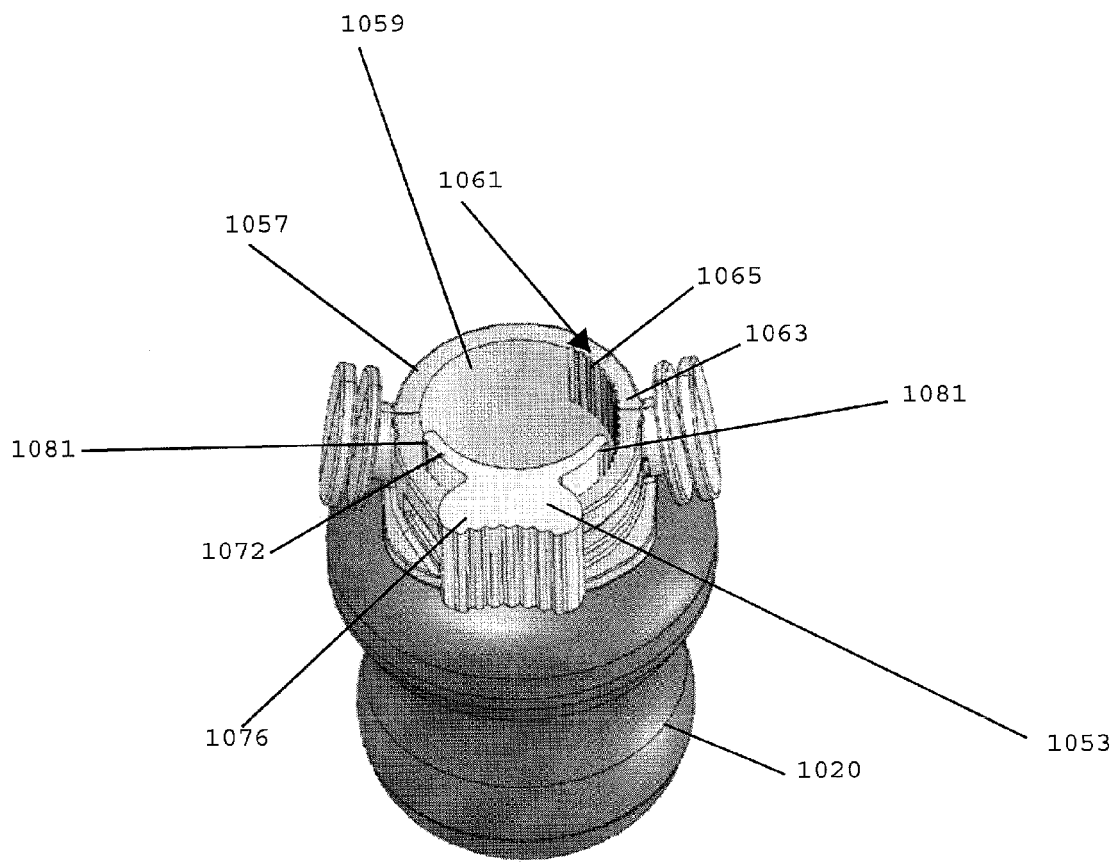
FIG. 16 is a perspective view of another embodiment of stability assembly.
Figure 17:
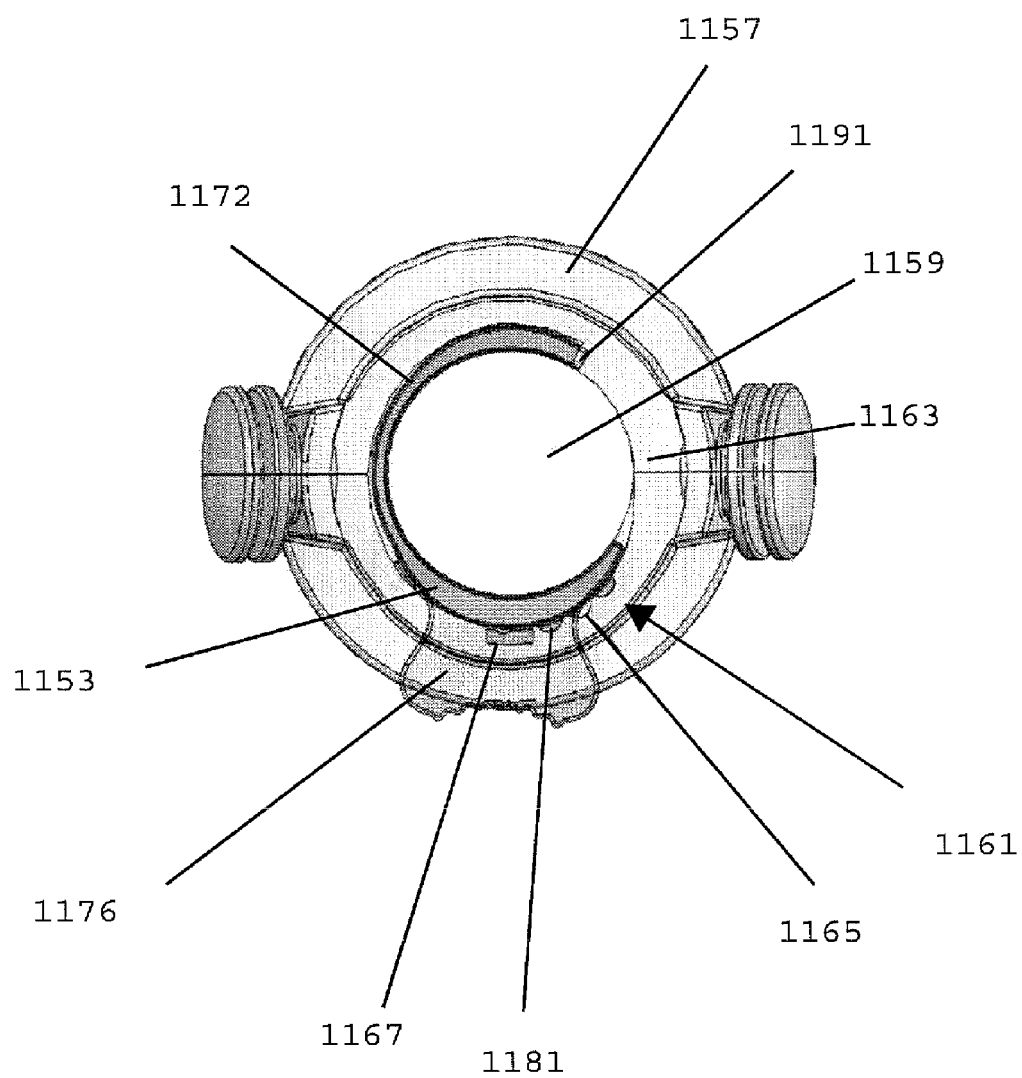
FIG. 17 is a top view of a base and cannula retention member of another embodiment of stability assembly.

With reference to FIGS. 7-17, stability assemblies having various embodiments of latch mechanism are illustrated. FIGS. 7-10 illustrate top views of various embodiments of stability assemblies having latch mechanisms with a first interface surface on an outer surface of a base, and a second interface surface on the cannula retention member. FIGS. 11-14 illustrate various embodiments of stability assembly having latch mechanisms with a first interface surface on a flange of the base, and a second interface surface on the cannula retention member. FIGS. 15-17 illustrate top views of various embodiments of stability assemblies having latch mechanisms with a first interface surface on it inner surface of the base and a second interface surface on the cannula retention member. It is contemplated that various aspects of each of these embodiments can be combined with various aspects of others of these embodiments to form different embodiments of stability assembly within the scope of this application.

Figure 7:
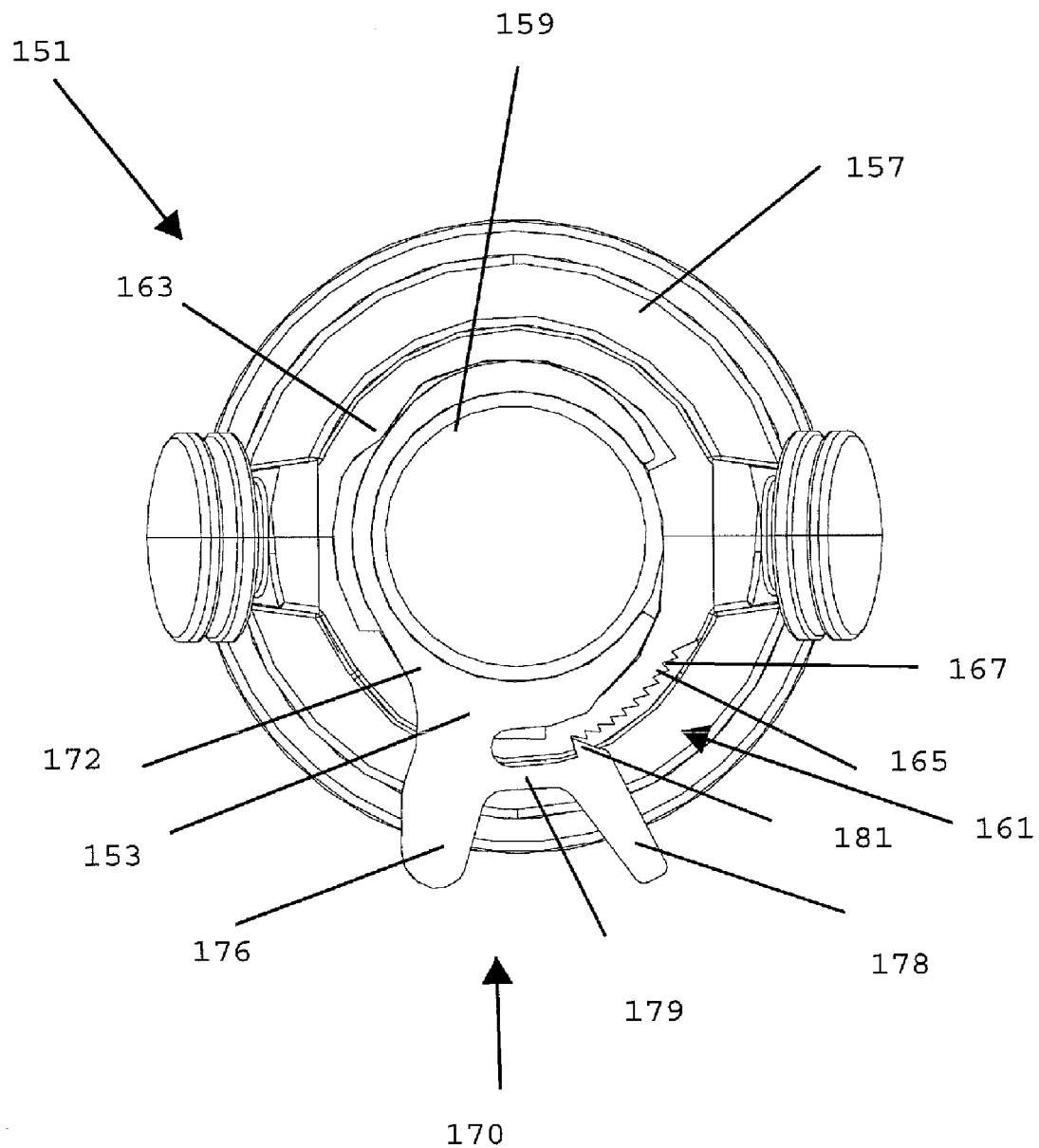
FIG. 7 is a top view of a base and cannula retention member of another embodiment of stability assembly.

With reference to FIG. 7, an embodiment of stability assembly 151 is illustrated that comprises a base 157 and a cannula retention member 153. Similar to the embodiment of FIGS. 1-6, in the embodiment illustrated in FIG. 7, the base comprises a passage 159 defining an inner surface thereof and a constriction such as a ramp surface 163. In some embodiments, the base 157 can comprise a ledge or stop 191 to limit rotation of the cannula retention member 153. As illustrated, the cannula retention member 153 comprises an annular loop portion 172 and a lever portion 170. As illustrated, the lever portion 170 comprises an actuation lever 176, a latch lever 178, and a flexible rib 179 pivotably connecting the latch lever 178 to the actuation lever 176. An interface surface such as a pawl 181 can be disposed on an end of the latch lever 178.

In the embodiment illustrated in FIG. 7, an interface surface on the base 157 comprises a ratchet 161 having a plurality of ramps. Each ramp comprises an inclined surface 165 and a detent 167. In operation, as the cannula retention member 153 is advanced from a first position in which a cannula can be inserted or moved within the passage 159 to a second position in which the cannula is retained by the passage 159, the pawl 181 is advanced over one or more inclined surfaces 165 and into one or more detents 167 of the ratchet 161. The detents 167 maintain the position of the cannula retention member 153 with respect to the base 157 once a desired position has been achieved. To release a cannula from within the passage 159, a user can disengage the pawl 181 from the ratchet 161 by pivoting the latch lever 178 with respect to the actuation lever 176, such as by pinching the levers 176, 178 between a thumb and forefinger. With the pawl 181 disengaged from the ratchet 161, the cannula retention member 153 can be returned to a first position, and the cannula moved or withdrawn from the passage 159.

Advantageously, a ratchet latch mechanism allows a user to selectively restrain the cannula retention mechanism in a plurality of positions with respect to the base. Thus, a ratchet latch mechanism can allow adjustment of the amount of clamping force as desired by the user. Further, a ratchet latch mechanism is intuitive to use and can provide tactile and audible feedback to the user.

In various embodiments a stability assembly having a ratchet latch mechanism, the shape of the ramps can vary to retain a particular desired resistance and feel to the locking and unlocking actuation. In some embodiments, an initial ramp of a ratchet mechanism can be enlarged relative to other steps to reduce initial actuation and or identify the initial or start position of the retention member. Furthermore, the location of the ramps of a ratchet can be varied to provide different clamping forces or different cannula sizes or reversed between the lever and the base.

Figure 8:
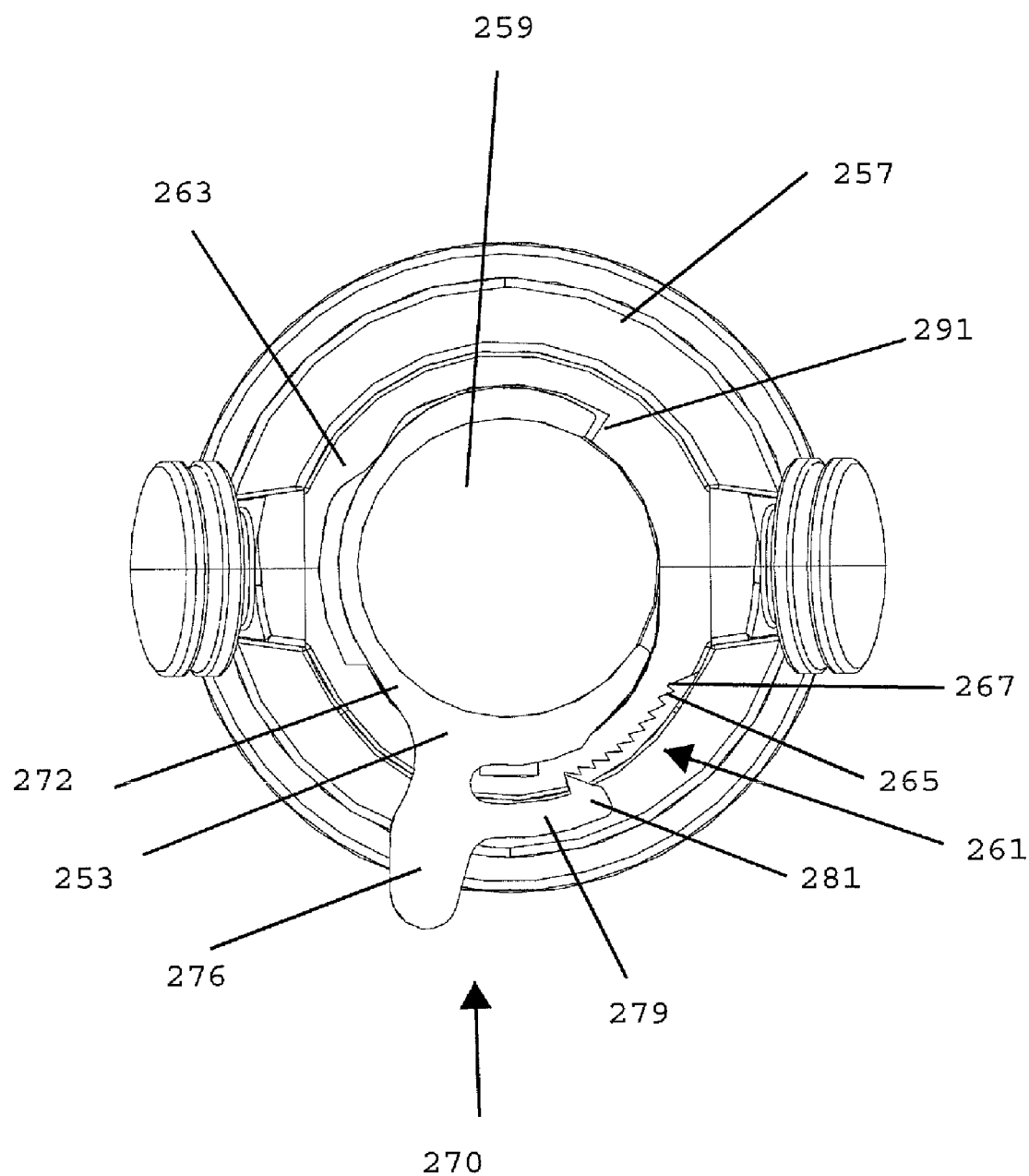
FIG. 8 is a top view of a base and cannula retention member of another embodiment of stability assembly.

With reference to FIG. 8, some embodiments of stability assembly do not include a latch lever in the latch mechanism. As illustrated in FIG. 8, an embodiment of stability assembly comprises a base 257 and a cannula retention member 253. Similar to the embodiment of FIGS. 1-6, in the embodiment illustrated in FIG. 8, the base comprises a passage 259 defining an inner surface thereof, and a constriction such as a ramped surface 263. In some embodiments, the base 257 can comprise a ledge or stop 291 to limit rotation of the cannula retention member 253. Likewise as illustrated, the cannula retention member 253 comprises an annular loop portion 272, and a lever portion 270. As illustrated, the lever portion 270 comprises an actuation lever 276, an interface surface such as a pawl 281, and a flexible rib 279 pivotably connecting the interface surface 281 to the actuation lever 276.

With continued reference to FIG. 8, an interface surface on the base 257 comprises a ratchet 261 having a plurality of ramps. Each ramp comprises an inclined surface 265 and a detent 267. Operation of the stability assembly of FIG. 8 is substantially similar to the embodiment described above with respect to FIG. 7. However, to disengage the pawl to a one from the ratchet 261, a user can pull the pawl 281 away from the ratchet 261 such as by pulling on the pawl 281 radially outward with a finger.

Figure 9:
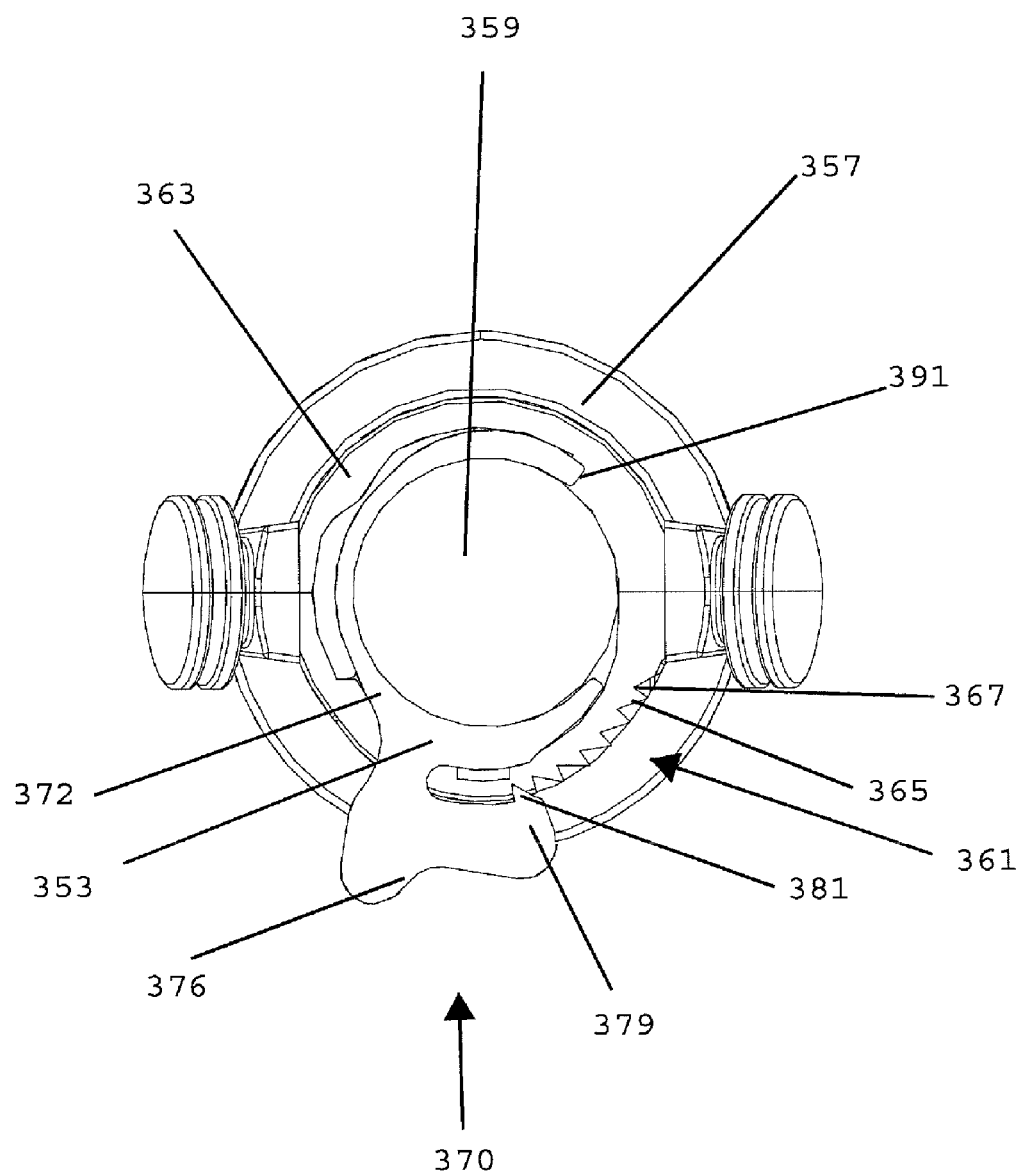
FIG. 9 is a top view of a base and cannula retention member of another embodiment of stability assembly.

With reference to FIG. 9, as noted above, some embodiments of stability assembly with a ratchet latch mechanism include different geometries for the ramp steps of the ratchet. As illustrated in FIG. 9, an embodiment of stability assembly comprises a base 357, and a cannula retention member 353. Similar to the embodiment of FIGS. 1-6, in the embodiment illustrated in FIG. 9, the base comprises a passage 359 defining an inner surface thereof, and a constriction such as a ramped surface 363. In some embodiments, the base 357 can comprise a ledge or stop 391 to limit rotation of the cannula retention member 353. Likewise as illustrated, the cannula retention member 353 comprises an annular loop portion 372, and a lever portion 370. As illustrated, the lever portion 370 comprises an actuation lever 376, an interface surface such as a pawl 381, and a flexible rib 379 pivotably connecting the interface surface 381 to the actuation lever 376.

With continued reference to FIG. 9, an interface surface on the base 357 comprises a ratchet 361 having a plurality of ramps. Each ramp comprises an inclined surface 365 and a detent 367. Operation of the stability assembly of FIG. 9 is substantially similar to the embodiment described above with respect to FIG. 8, as the pawl 381 of the embodiment illustrated in FIG. 9 can be directly disengaged by a user. In the embodiment of FIG. 9, the ratchet 361 includes fewer, relatively larger ramps, as compared with the embodiment of FIG. 8. Thus, the embodiment of FIG. 9 provides fewer discrete detented positions for the cannula retention member 353.

Figure 10:
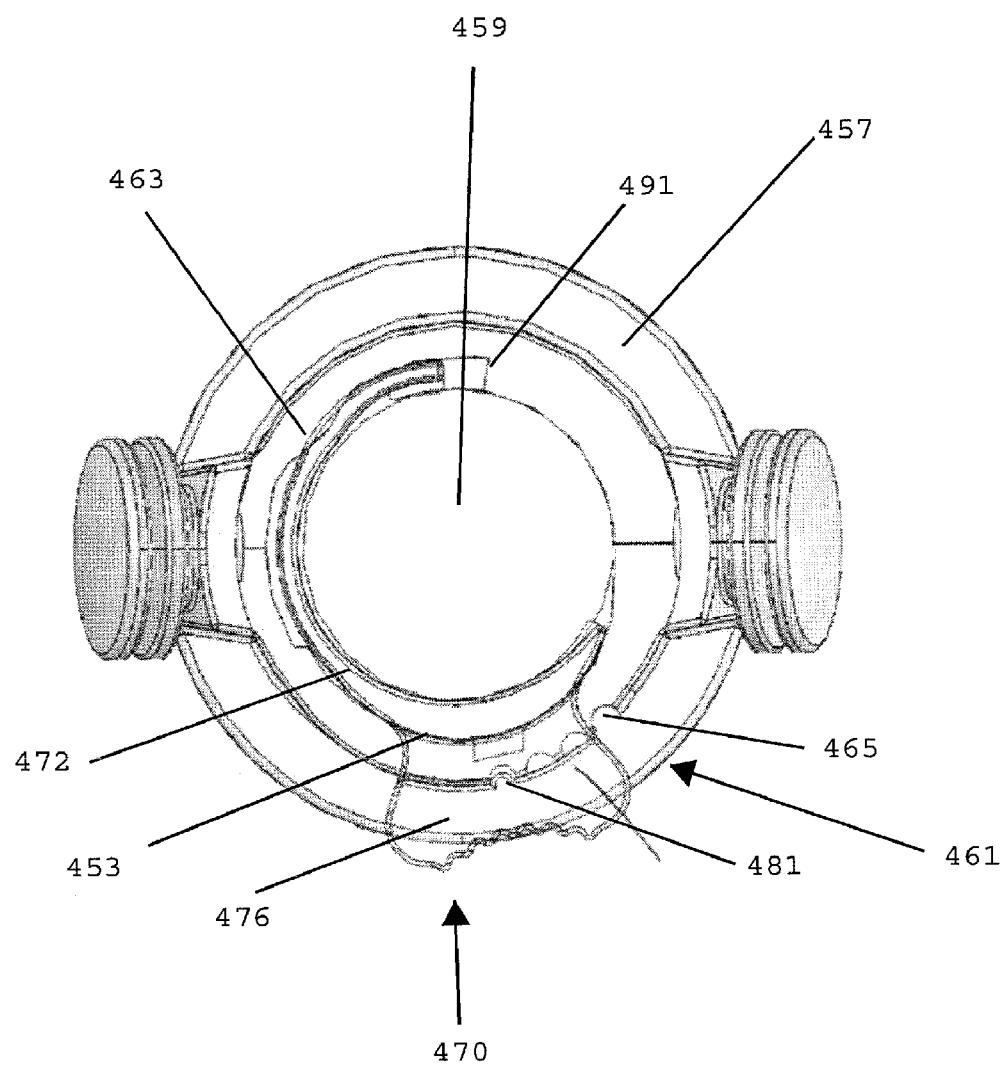
FIG. 10 is a top view of a base and cannula retention member of another embodiment of stability assembly.

With reference to FIG. 10, as noted above, some embodiments of stability assembly with a ratchet latch mechanism include different geometries for the ramp steps and pawl of the latch mechanism. As illustrated in FIG. 10, an embodiment of stability assembly comprises a base 457, and a cannula retention member 453. Similar to the embodiment of FIGS. 1-6, in the embodiment illustrated in FIG. 10, the base comprises a passage 459 defining an inner surface thereof, and a constriction such as a ramped surface 463. In some embodiments, the base 457 can comprise a ledge or stop 491 to limit rotation of the cannula retention member 453. Likewise as illustrated, the cannula retention member 453 comprises an annular loop portion 472, and a lever portion 470. As illustrated, the lever portion 470 comprises an actuation lever 476 and an interface surface such as a contoured protrusion 481 formed on the actuation lever 476.

With continued reference to FIG. 10, an interface surface on the base 457 comprises a ratchet 461 having a plurality of recesses 465. Each recess 465 is contoured to receive the protrusion 481 on the retention member 453. Desirably, the recesses 465 and protrusion 481 are contoured such that they facilitate engagement and disengagement as the cannula retention member 453 is rotated with respect to the base 457. For example, in the illustrated embodiment, the protrusion 481 comprises a generally semi-circular profile, and the recesses 465 each comprises a mating generally circular profile. It is contemplated that in other embodiments, other curvilinear or straight mating profiles can form the interface surfaces of the stability assembly of FIG. 10. Operation of the stability assembly of FIG. 10 is substantially similar to the embodiment described above with respect to FIG. 9 However, in the embodiment of FIG. 10, the contoured interface surfaces allow rotation of the retention member 453 with respect to the base 457 without movement of a pawl. Thus, the embodiment of FIG. 10 can provides multiple ratchet-like stops with a different user interface feel than a pawl and ratchet interface.

With reference to FIGS. 11-14, embodiments of stability assembly are illustrated with a latch mechanism having an interface surface positioned on a flange of the base. FIG. 11A illustrates an exploded perspective view of one embodiment a stability assembly, FIG. 11B illustrates a perspective view of the base of the stability assembly of FIG. 11A, and FIG. 11C illustrates a top view of the base and retention member of the stability assembly of FIG. 11A. FIG. 12A illustrates an exploded perspective view of one embodiment a stability assembly, FIG. 12B illustrates a perspective view of the retention member of the stability assembly of FIG. 12A in a first position, FIG. 12C illustrates the retention member of the stability assembly of FIG. 12A in a second position, and FIG. 12D illustrates a top view of the base and retention member of the stability assembly of FIG. 12A. FIG. 13 illustrates a perspective view of another embodiment of stability assembly having an interface service positioned on a flange of the base. FIG. 14 illustrates a perspective view of another embodiment of stability assembly having an interface surface positioned on a flange of the base.

Figure 11A:
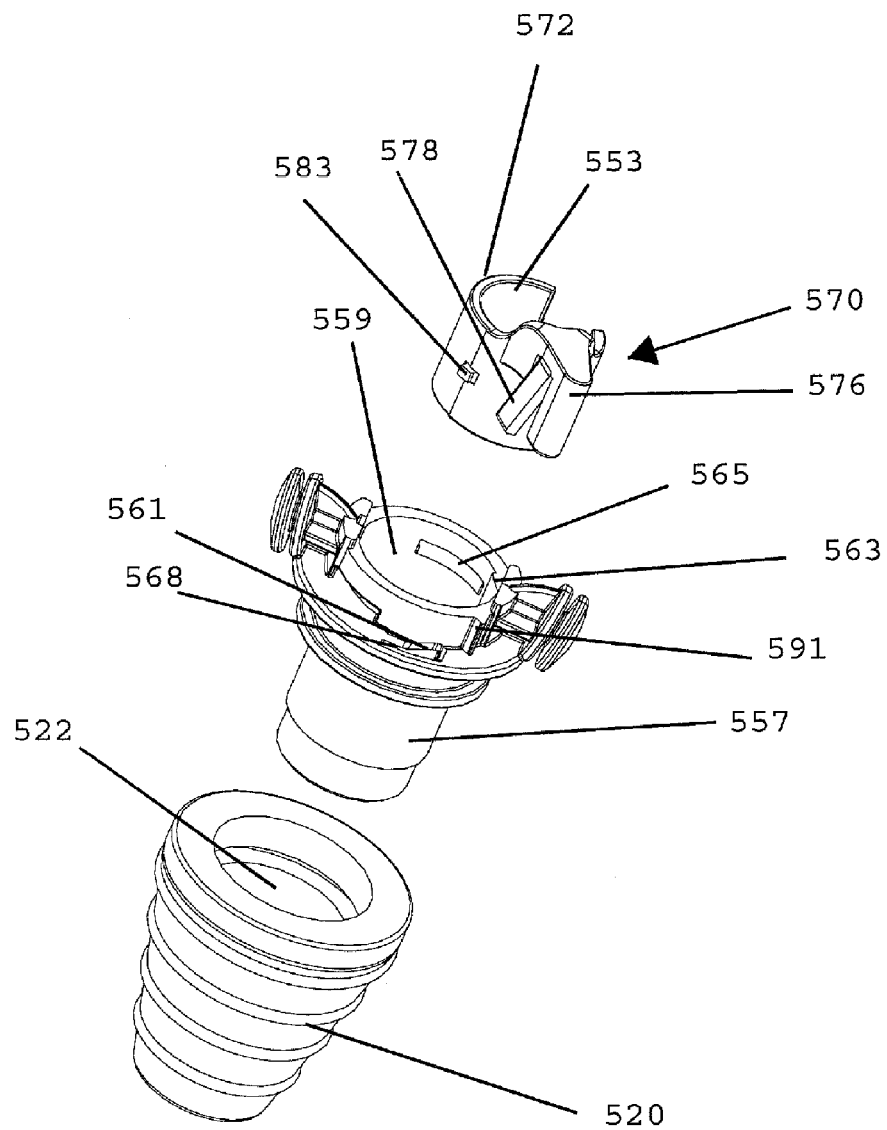
FIG. 11A is an exploded perspective view of an embodiment of stability assembly.
Figure 11B:
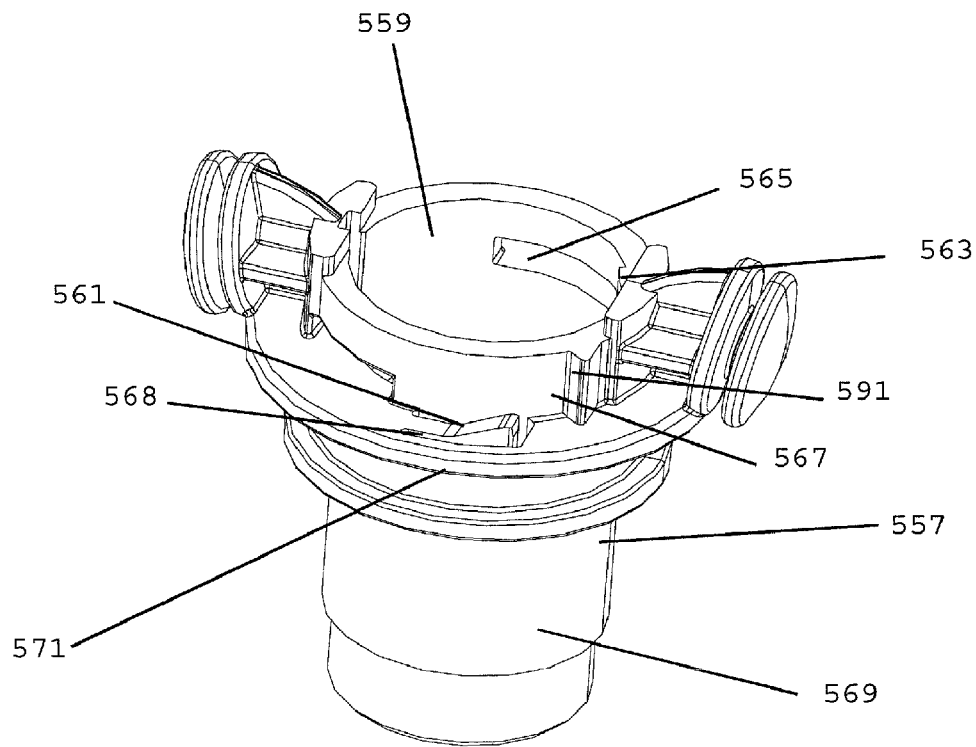
FIG. 11B is a perspective view of the base of the stability assembly of FIG. 11A.
Figure 11C:
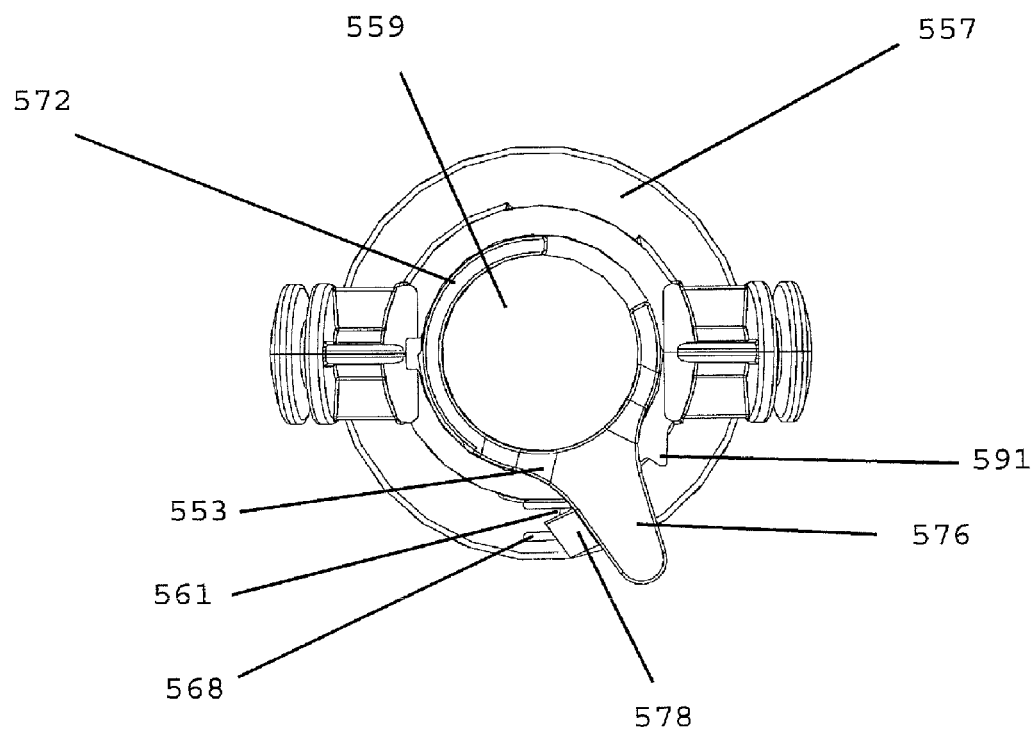
FIG. 11C is a top view of the base and cannula retention member of the stability assembly of FIG. 11A.
Figure 12A:
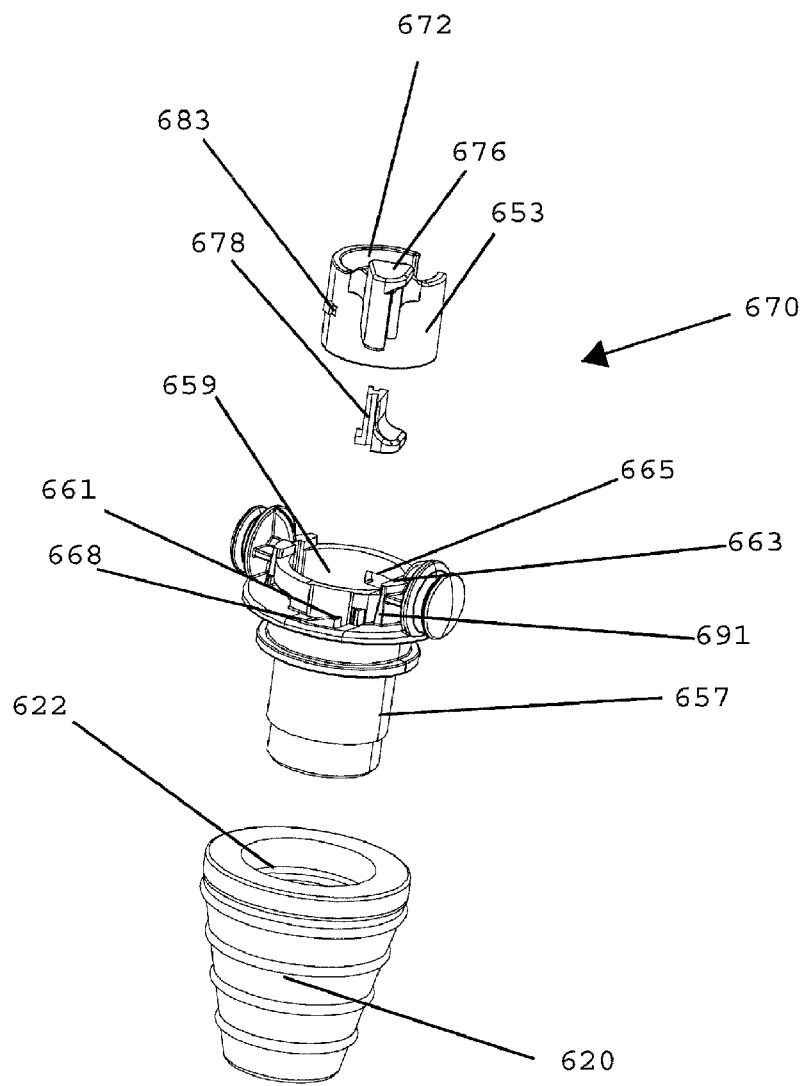
FIG. 12A is an exploded perspective view of an embodiment of stability assembly.
Figure 12B:
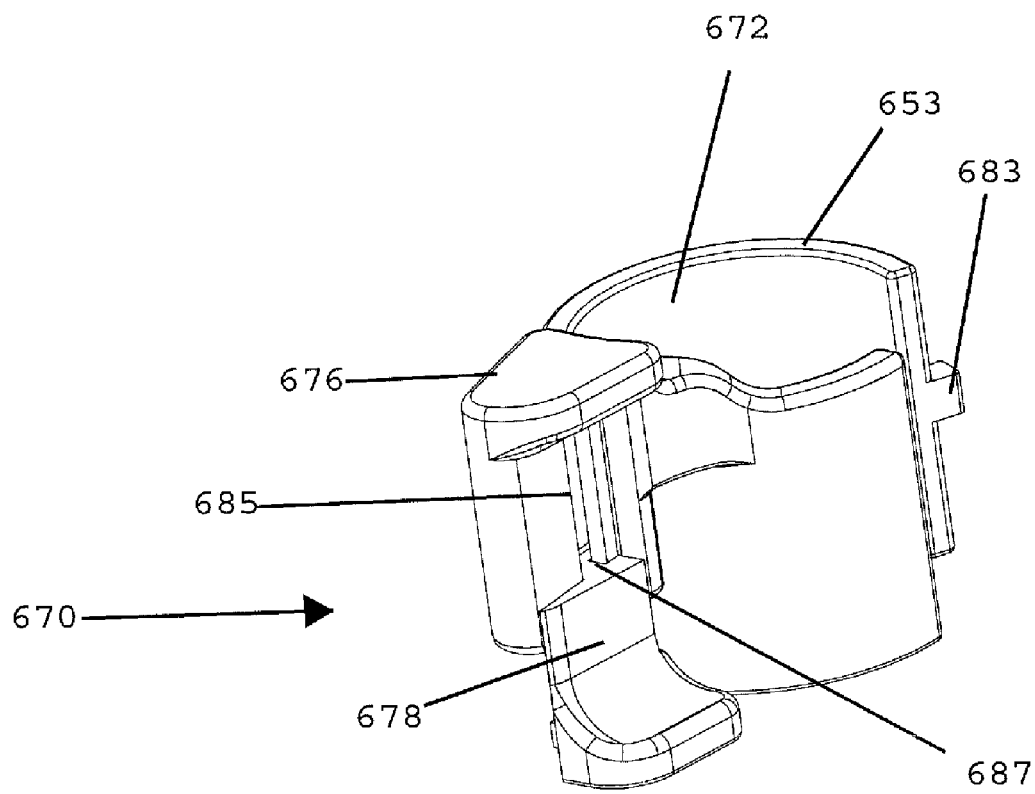
FIG. 12B is a perspective view of the cannula retention member of the stability assembly of FIG. 12A with a lever assembly in a first position.
Figure 12C:
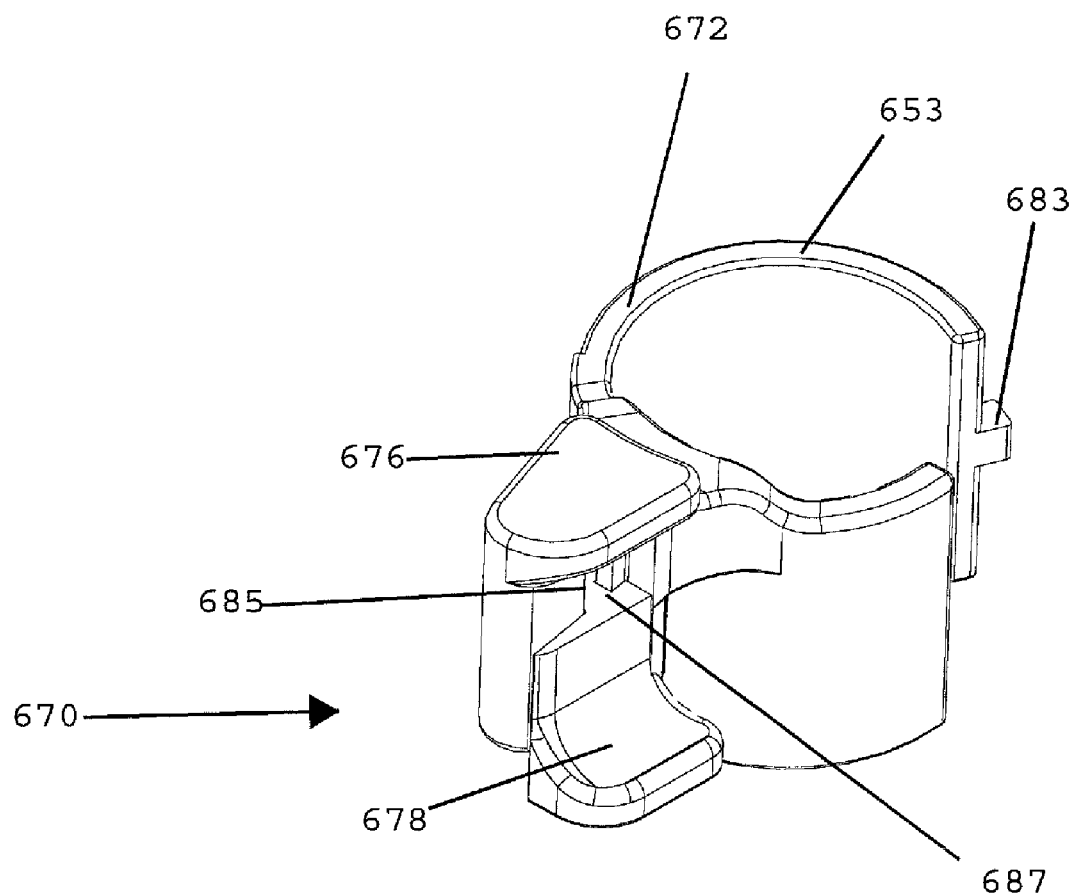
FIG. 12C is a perspective view of the cannula retention member of the stability assembly of FIG. 12A with a lever assembly in a second position.
Figure 12D:
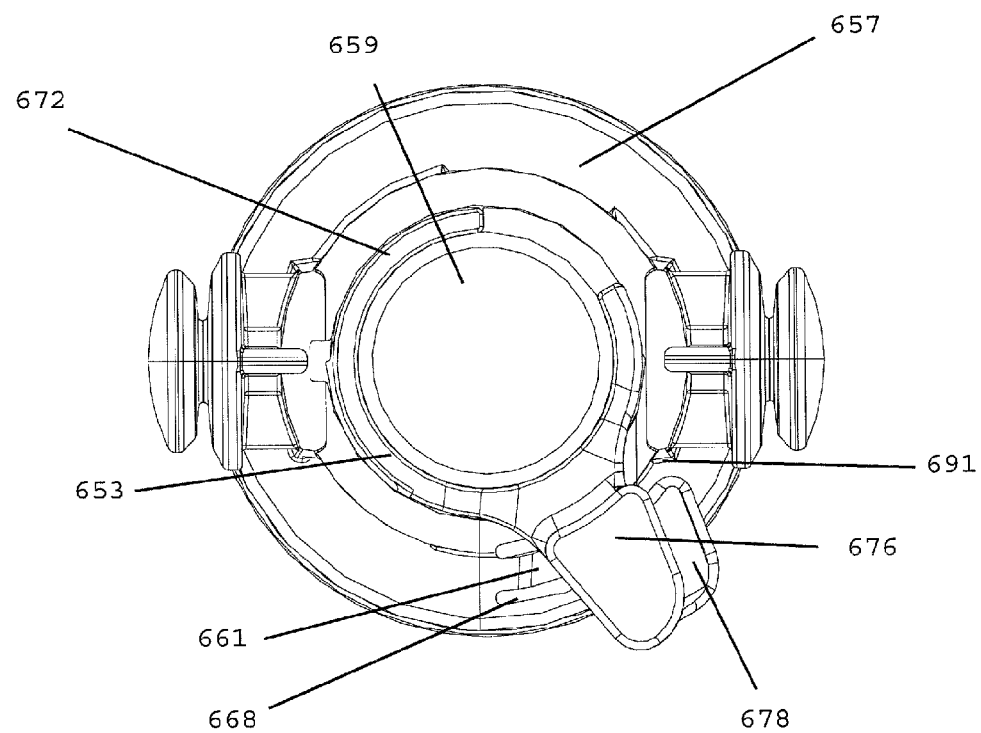
FIG. 12D is a top view of the base and cannula retention member of the stability assembly of FIG. 12A.

With reference to FIGS. 11A-11C, similar to the embodiment of FIGS. 1-6, in the embodiment illustrated in FIG. 11 (which includes FIGS. 11A-11C), the stability assembly comprises a stability member 520 having a lumen 522 extending therethrough, a base 557 comprising a passage 559 defining an inner surface thereof, a constriction such as a ramped surface 563, and a retention slot 565. In some embodiments, the base 557 can comprise a ledge or stop 591 to limit rotation of the cannula retention member 553. Likewise as illustrated, the cannula retention member 553 comprises an annular loop portion 572, and a lever portion 570. As illustrated, the lever portion 570 comprises an actuation lever 576 and a latch lever 578 pivotably coupled to the actuation lever 576. The annular loop portion 572 can comprise a retention tab 583 to maintain the longitudinal position of the retention member 553 with respect to the base 557.

With continued reference to FIG. 11, an interface surface on the base 557 comprises a ramp 561 positioned on a flange 571 of the base 557. In the illustrated embodiment, the flange 571 separates a proximal portion 567 of the base 557 from a distal portion 569 of the base. In some embodiments, the ramp 561 can be flexible relative to the flange 571. For example, as illustrated, the ramp 561 can have a slot 568 adjacent to it such that the ramp 561 can flex with respect to the flange 571. In other embodiments, other arrangements can enhance the flexibility of the ramp 561. This flexibility can allow the latch lever 578 to easily engage and disengage a detented surface of the ramp 561.

Operation of the stability assembly of FIG. 11 is substantially similar to that of the stability assembly of FIGS. 1-6. A user can advance the retention member 553 from the first position towards the second position, thereby advancing the latch lever 578 over the ramp 561. In some embodiments, flexibility of the ramp 561 can facilitate this advancement by allowing the ramp 561 to move longitudinally distally with respect to the base. To disengage the latch lever 578 from the ramp 561, the user can pivot the latch lever 578 toward the actuation lever 576, such as by squeezing the levers 576, 578 toward one another between the user's thumb and finger.

With reference to FIGS. 12A-12D, similar to the embodiment of FIGS. 1-6, in the embodiment illustrated in FIG. 12 (which includes FIGS. 12A-12D), the stability assembly comprises a stability member 620 having a lumen 622 extending therethrough, a base 657 comprises a passage 659 defining an inner surface thereof, a constriction such as a ramped surface 663, and a retention slot 665. In some embodiments, the base 657 can comprise a ledge or stop 691 to limit rotation of the cannula retention member 653. Likewise as illustrated, the cannula retention member 653 comprises an annular loop portion 672, and a lever portion 670. As illustrated, the lever portion 670 comprises an actuation lever 676 and a latch lever 678 slidably coupled to the actuation lever 676. The annular loop portion 672 can comprise a retention tab 683 to maintain the longitudinal position of the retention member 653 with respect to the base 657.

With continued reference to FIG. 12, similar to the stability assembly of FIG. 11, an interface surface on the base 657 comprises a ramp 661 positioned on a flange 671 of the base 657, which can be configured to be flexible, such as with an adjacent slot 668. The interface surface on the retention member 653 comprises a two-piece sliding lever assembly 670. The lever assembly 670 comprises an actuation lever 676, and a latch lever 678 slidably disposed with respect to the actuation lever 676. The actuation lever 676 can have a track 685 formed therein, and the latch lever 678 can have a profiled surface 687 adapted to slidably engage the track 685. In other embodiments, other sliding arrangements and track geometries such as a rounded track and rounded mating profile can be provided. FIG. 12B illustrates the latch lever 678 in a lowered position such that it can interfere with a detent of the ramp 661 positioned on the flange 671 of the base 657. FIG. 12C illustrates the latch lever 678 in a raised position such that it does not interfere with the detent of the ramp 661 on the flange 671 of the base 657.

Operation of the stability assembly of FIG. 12 is substantially similar to that of the stability assembly of FIG. 11. A user can advance the retention member 653 from the first position towards the second position, thereby advancing the latch lever 678 over the ramp 661. In some embodiments, flexibility of the ramp 661 can facilitate this advancement. To disengage the latch lever 678 from the ramp 661, the user can slide the latch lever 678 toward the actuation lever 676, such as by squeezing the levers 676, 678 in the user's thumb and forefinger. Thus, once the retention member 653 has been rotated to second position, the latch lever 678 in the lowered position can retain the retention member 653 in the second position, while raising the latch lever by sliding it relative to the actuation lever allows the retention member 653 to be returned to the first position. In some embodiments, the lever assembly 670 can comprise a biasing member such as a spring to bias the latch lever 678 towards the lower position.

With reference to FIG. 13, similar to the embodiment of FIGS. 1-6, in the embodiment illustrated in FIG. 13, the stability assembly comprises a stability member 720, a base 757 comprising a passage 759 defining an inner surface thereof, and a retention slot 765. Likewise as illustrated, the cannula retention member 753 comprises an annular loop portion 772, and a lever portion 770. As illustrated, the lever portion 770 comprises an actuation lever 776. The actuation lever 776 comprises a latch portion 778 formed therewith. The actuation lever 776 can be coupled to the annular loop portion 772 by a flexible rib 779. The annular loop portion 772 can comprise a retention tab 783 to maintain the longitudinal position of the retention member 753 with respect to the base 757.

With continued reference to FIG. 13, similar to the stability assembly of FIG. 11, an interface surface on the base 757 comprises a ramp 761 positioned on a flange 771 of the base 757, which can be configured to be flexible, such as with an adjacent slot 768. The interface surface on the retention member 753 comprises a surface of the latch portion 778.

Operation of the stability assembly of FIG. 13 is substantially similar to that of the stability assembly of FIG. 11. A user can advance the retention member 753 from the first position towards the second position, thereby advancing the latch portion 778 over the ramp 761. In some embodiments, flexibility of the ramp 761 can facilitate this advancement. To disengage the latch portion 778 from the ramp 761, the user can pivot the latch portion 778 away from the ramp 761, such as by torquing the actuation lever 776 to cause a pivot motion about the flexible rib 779.

With reference to FIG. 14, similar to the embodiment of FIGS. 1-6, in the embodiment illustrated in FIG. 14, the stability assembly comprises a stability member 820, a base 857 comprising a passage 859 defining an inner surface thereof, and a retention slot 865. Likewise as illustrated, the cannula retention member 853 comprises an annular loop portion 872, and a lever portion 870. As illustrated, the lever portion 870 comprises an actuation lever 876. The actuation lever 876 comprises a latch portion 878 and flexible portion 879 formed therewith. In the illustrated embodiment, the flexible portion 879 can be formed by a relief slot in the lever portion. In other embodiments, it is contemplated that other flexibility enhancing geometries, such as a relatively thin segment of material, can be used in the flexible portion. The annular loop portion 872 can comprise a retention tab 883 to maintain the longitudinal position of the retention member 853 with respect to the base 857.

With continued reference to FIG. 14, similar to the stability assembly of FIG. 11, an interface surface on the base 857 comprises a ramp 861 positioned on a flange 871 of the base 857, which can be configured to be flexible, such as with an adjacent slot 868. The interface surface on the retention member 853 comprises a surface of the latch portion 878.

Operation of the stability assembly of FIG. 14 is substantially similar to that of the stability assembly of FIG. 11. A user can advance the retention member 853 from the first position towards the second position, thereby advancing the latch portion 878 over the ramp 861. In some embodiments, flexibility of the ramp 861 can facilitate this advancement. To disengage the latch portion 878 from the ramp 861, the user can pivot the latch portion 878 away from the ramp 861, such as by flexing the latch portion 878 of the actuation lever about the flexible portion 879.

With reference to FIGS. 15-17, embodiments of stability assembly are illustrated with a latch mechanism having an interface surface positioned on a inner surface of the base. FIG. 15 illustrates a top view of a base and cannula retention member of a stability assembly. FIG. 16 illustrates a perspective view of another embodiment of stability assembly. FIG. 17 illustrates a top view of another embodiment of stability assembly.

With reference to FIG. 15, similar to the embodiment of FIGS. 1-6, in the embodiment illustrated in FIG. 15, the base 957 comprises a passage 959 defining an inner surface thereof, and a constriction such as a ramp surface 963. In some embodiments, the base 957 can comprise at least one ledge or stop 991 to limit rotation of the cannula retention member 953. As illustrated, the cannula retention member 953 comprises an annular loop portion 972, an actuation lever 976 formed adjacent a first end of the annular loop portion 972, and a latch lever portion 978 formed adjacent a second end of the annular loop portion 972. An interface surface such as a pawl 981 is disposed on an end of the latch lever 978.

In the embodiment illustrated in FIG. 15, an interface surface on the base 957 comprises a ratchet 961 having a plurality of ramps formed on an inner surface of the base 957. Each ramp comprises an inclined surface 965 and a detent 967. In operation, as the cannula retention member 953 is advanced from a first position in which a cannula can be inserted or moved within the passage 959 to a second position in which the cannula is retained by the passage 959, the pawl 981 is advanced over one or more inclined surfaces 965 and into one or more detents 967 of the ratchet 961. The detents 967 maintain the position of the cannula retention member 953 with respect to the base 957 once a desired position has been achieved. To release a cannula from within the passage 959, a user can disengage the pawl 981 from the ratchet 961 by compressing the latch lever 978 towards the passage 959. With the pawl 981 disengaged from the ratchet 961, the cannula retention member 953 can be returned to a first position, and a cannula moved or withdrawn from the passage 959.

With reference to FIG. 16, similar to the embodiment of FIGS. 1-6, in the embodiment illustrated in FIG. 16, the stability assembly comprises a stability member 1020, a base 1057 comprising a passage 1059 defining an inner surface thereof, and a cannula retention member 1053. The base 1057 comprises a constriction, which can be formed by an increased wall thickness portion 1063 forming a ramped inner wall. As illustrated, the cannula retention member 1053 comprises an annular loop portion 1072 and an actuation lever 1076. In the illustrated embodiment, the annular loop portion 1072 comprises a relatively small segment of a generally cylindrical member, however, it is contemplated that in other embodiments, a relatively larger segment could form the cannula retention member 1053. An interface surface such as at least one ridge 1081 is formed on a surface of the annular loop portion 1072. In the illustrated embodiment, a plurality of ridges 1081 is formed on a surface of the annular loop portion 1072.

In the embodiment illustrated in FIG. 16, an interface surface on the base 1057 comprises a ratchet 1061 having a plurality of ridges 1065 formed on an inner surface of the base 1057. The ridges 1065 on the base 1057 are configured to mate with the ridge 1081 on the cannula retention member 1053 in a plurality of secured positions. While in the illustrated embodiment, the interface surfaces comprise ridges 1065, 1081, it is contemplated that in other embodiments, other geometries of mating surface can be used such as angular protrusions or round protrusions and corresponding mating recesses.

In operation, as the cannula retention member 1053 is advanced from a first position in which a cannula can be inserted or moved within the passage 1059 to a second position in which the cannula is retained by the passage 1059, the ridge 1081 on the cannula retention member 1053 is advanced over the ridges 1065 on the base 1057. This mating of the ridges 1065, 1081 maintains the position of the cannula retention member 1053 with respect to the base 1057 once a desired position has been achieved. To release a cannula from within the passage 1059, a user can disengage the ridge 1081 from the ratchet 1061 by compressing the actuation lever 1076 radially inwardly with respect to the passage 1059. With the ridge 1081 disengaged from the ratchet 1061, the cannula retention member 1053 can be returned to a first position, and a cannula moved or withdrawn from the passage 1059.

With reference to FIG. 17, similar to the embodiment of FIGS. 1-6, in the embodiment illustrated in FIG. 17, the base 1157 comprises a passage 1159 defining an inner surface thereof, and a constriction such as a curved or ramped wall surface 1163. In some embodiments, the base 1157 can comprise at least one ledge or stop 1191 to limit rotation of the cannula retention member 1153. As illustrated, the cannula retention member 1153 comprises an annular loop portion 1172 and an actuation lever 1176. An interface surface such as a round protrusion 1181 is formed on a surface of the cannula retention member 1153.

In the embodiment illustrated in FIG. 17, an interface surface on the base 1157 comprises a ratchet 1161 having a plurality of generally curved recesses 1165 formed on an inner surface of the base 1157. The curved recesses 1165 on the base 1157 are configured to mate with the round protrusion 1181 on the cannula retention member 1153 in a plurality of secured positions. As illustrated, the ratchet 1161 further comprises an initial recess 1167 that is larger than the round protrusion 1181. This initial recess 1167 allows the position of the cannula retention member 1153 to be rotated slightly with respect to the base 1157 when the round protrusion 1181 is positioned in the initial recess 1167. Accordingly, the initial recess 1167 can provide a tactile indication to the user when the stability assembly is in a first position. In other embodiments, relatively large recesses can be positioned at other locations in the ratchet.

In operation, as the cannula retention member 1153 is advanced from a first position in which a cannula can be inserted or moved within the passage 1159 to a second position in which the cannula is retained by the passage 1159, the round protrusion 1181 is advanced out of the initial recess 1167 into one or more recesses 1165 of the ratchet 1161. The recesses 1165 maintain the position of the cannula retention member 1153 with respect to the base 1157 once a desired position has been achieved. To release a cannula from within the passage 1159, a user can disengage the round protrusion 1181 from the ratchet 1161 by compressing the actuation lever 1176 radially inwardly with respect to the passage 1159. With the round protrusion 1181 disengaged from the ratchet 1161, the cannula retention member 1153 can be returned to a first position in the initial recess 1167, and a cannula moved or withdrawn from the passage 1159.

Stability Assemblies for Threaded and Ribbed Cannulae

Figure 18A:
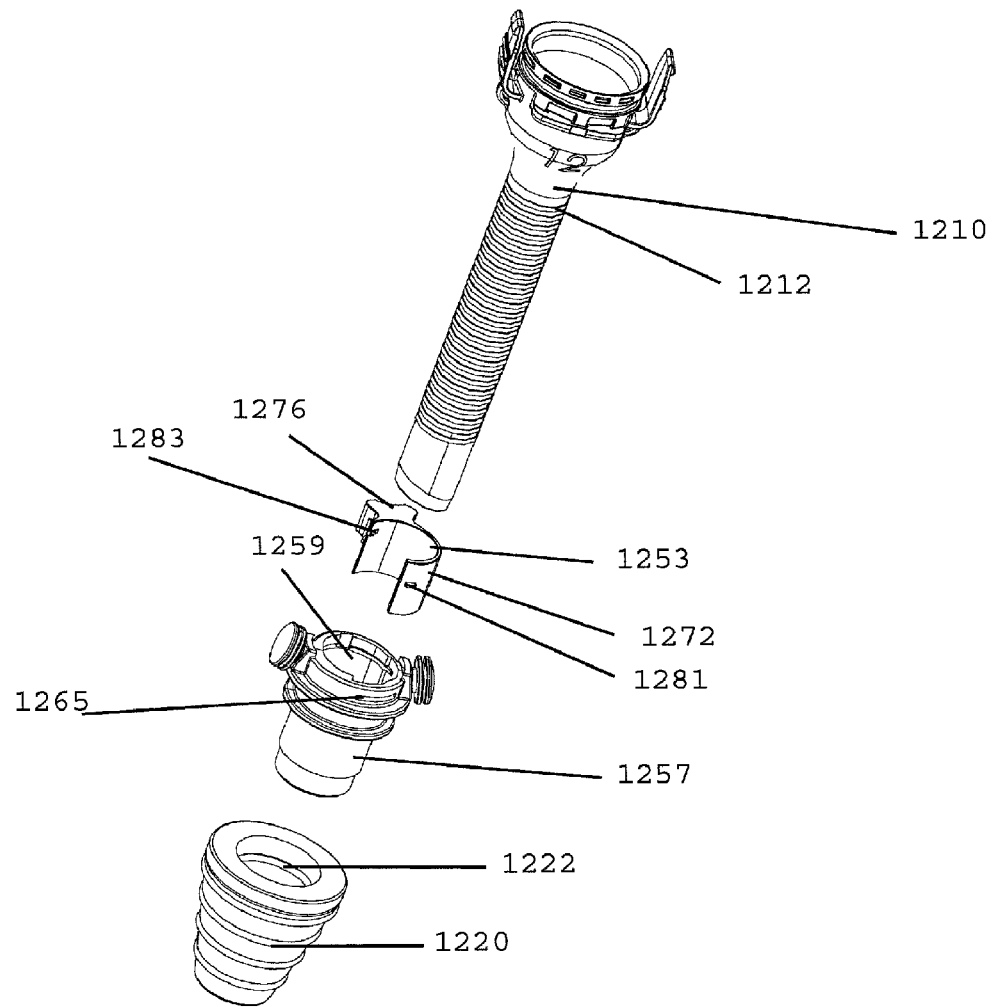
FIG. 18A is an exploded perspective view of a another embodiment of stability assembly with a ribbed cannula.
Figure 18B:
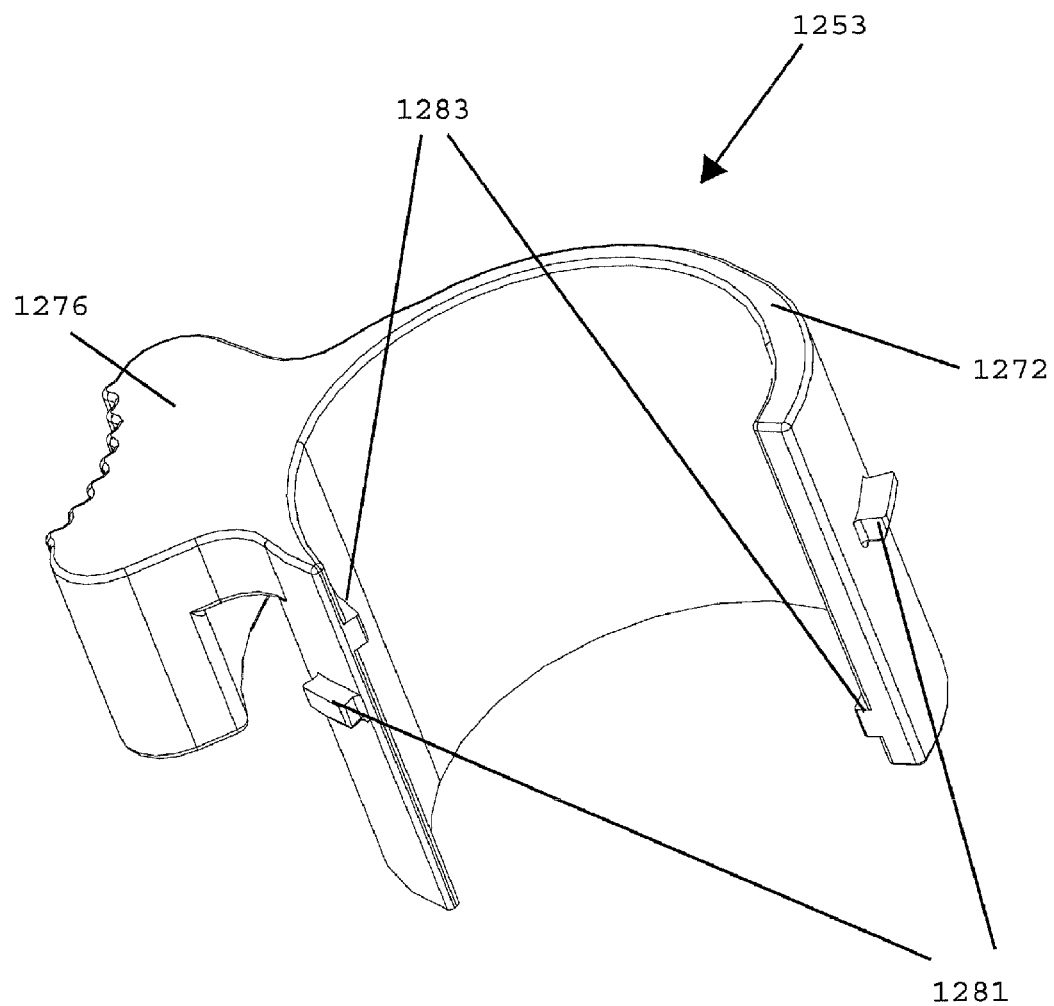
FIG. 18B is a perspective view of a cannula retention member of the stability assembly of FIG. 18A.
Figure 18C:
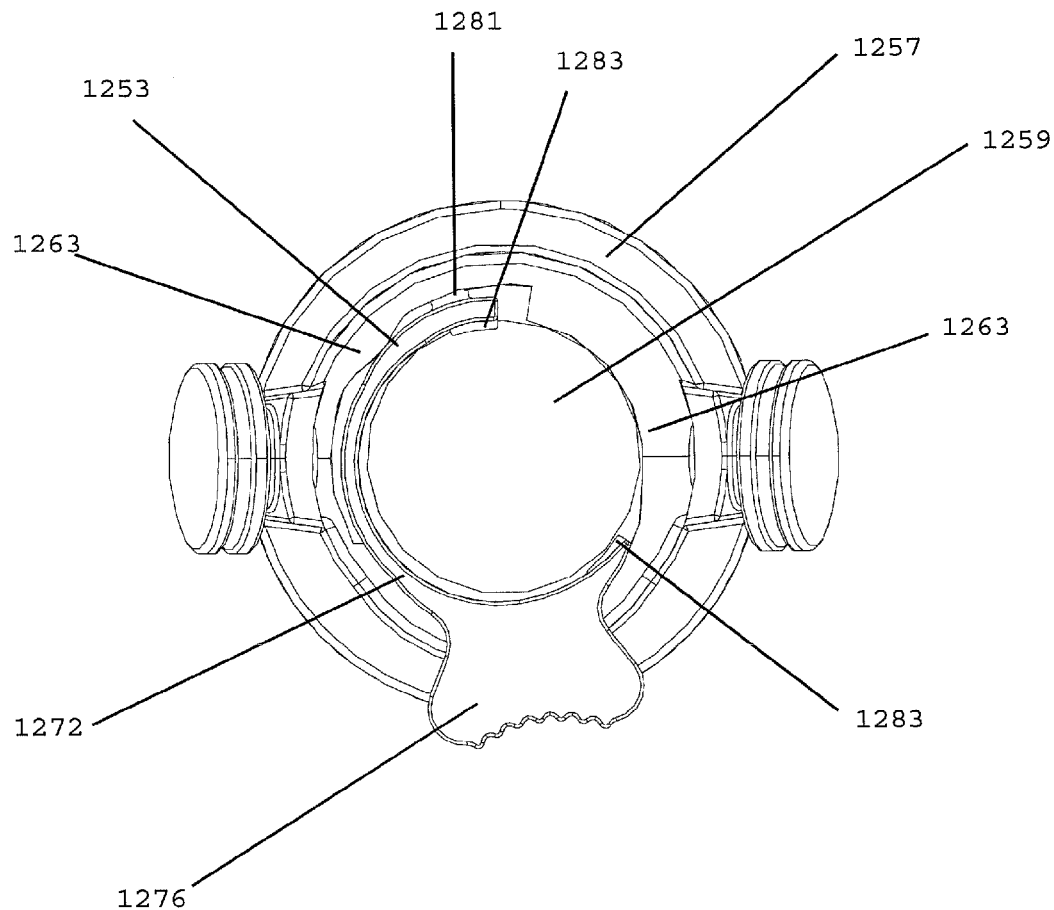
FIG. 18C is a top view of a base and the cannula retention member of the stability assembly of FIG. 18A.
Figure 19A:
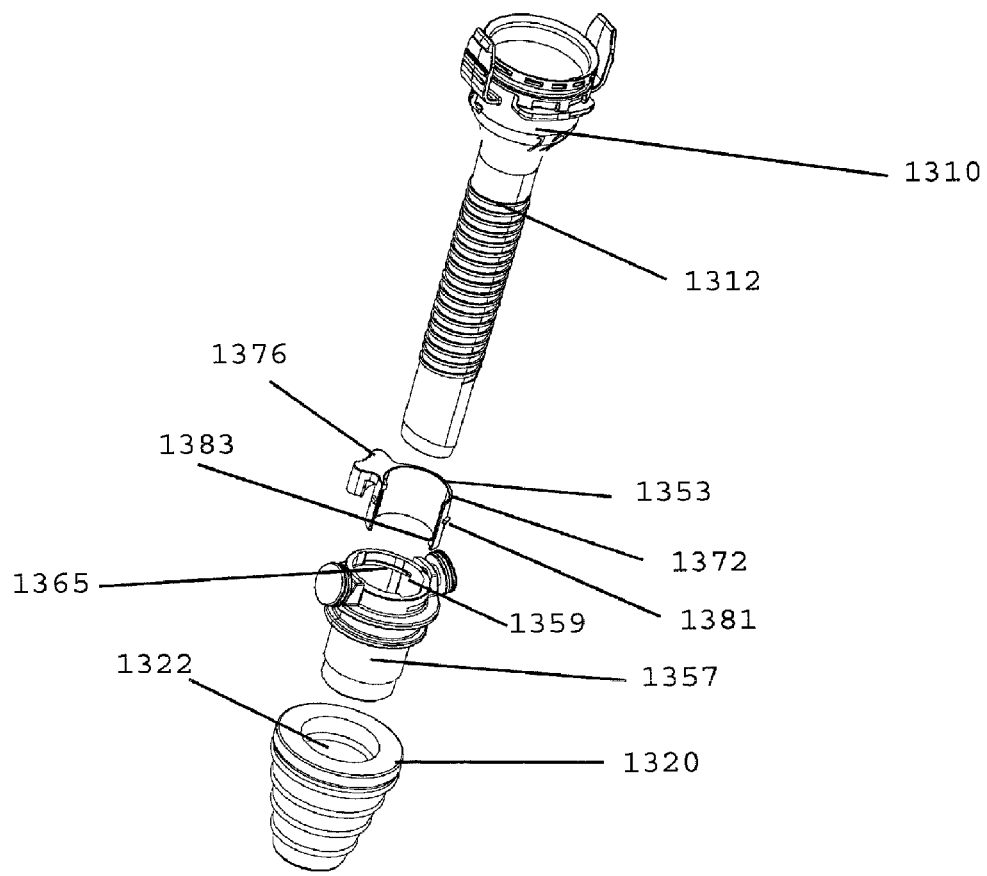
FIG. 19A is an exploded perspective view of another embodiment of stability assembly with a threaded cannula.
Figure 19B:
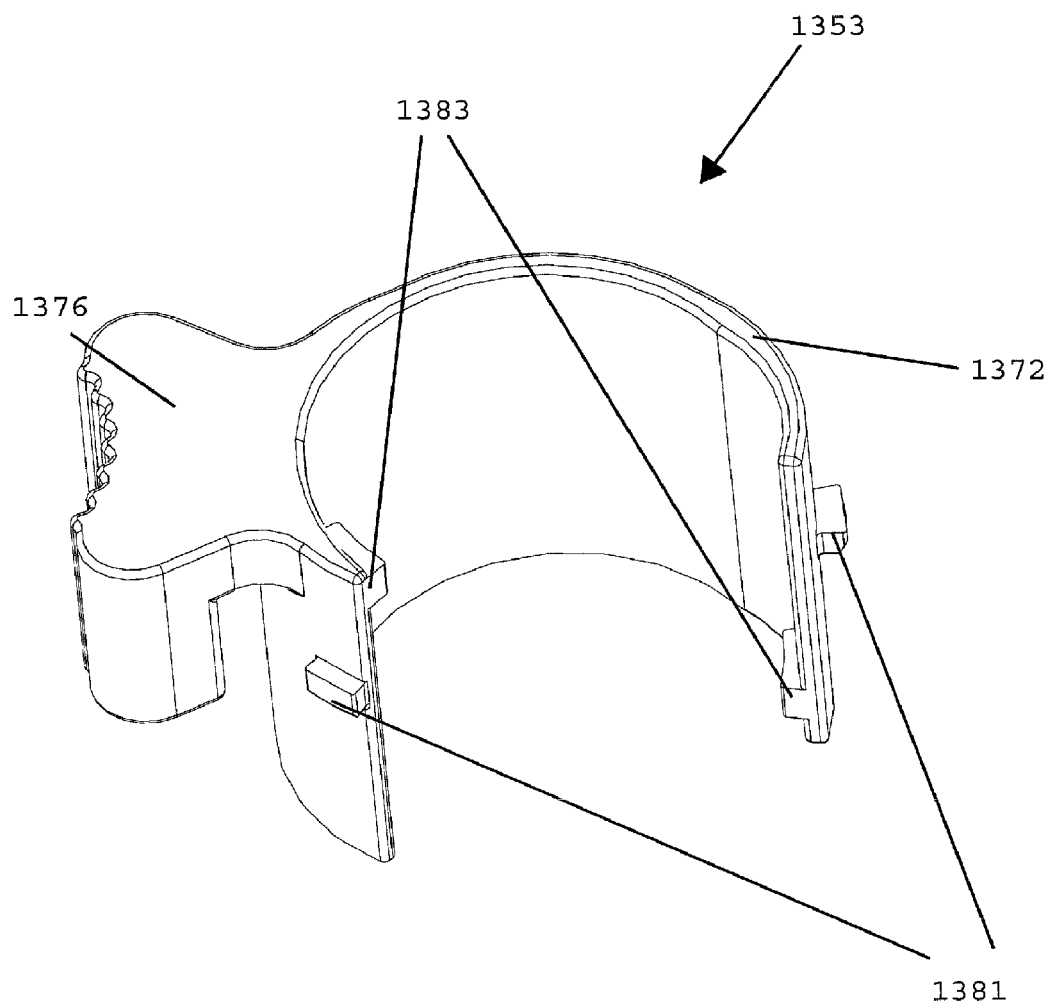
FIG. 19B is a perspective view of a cannula retention member of the stability assembly of FIG. 19A.
Figure 19C:
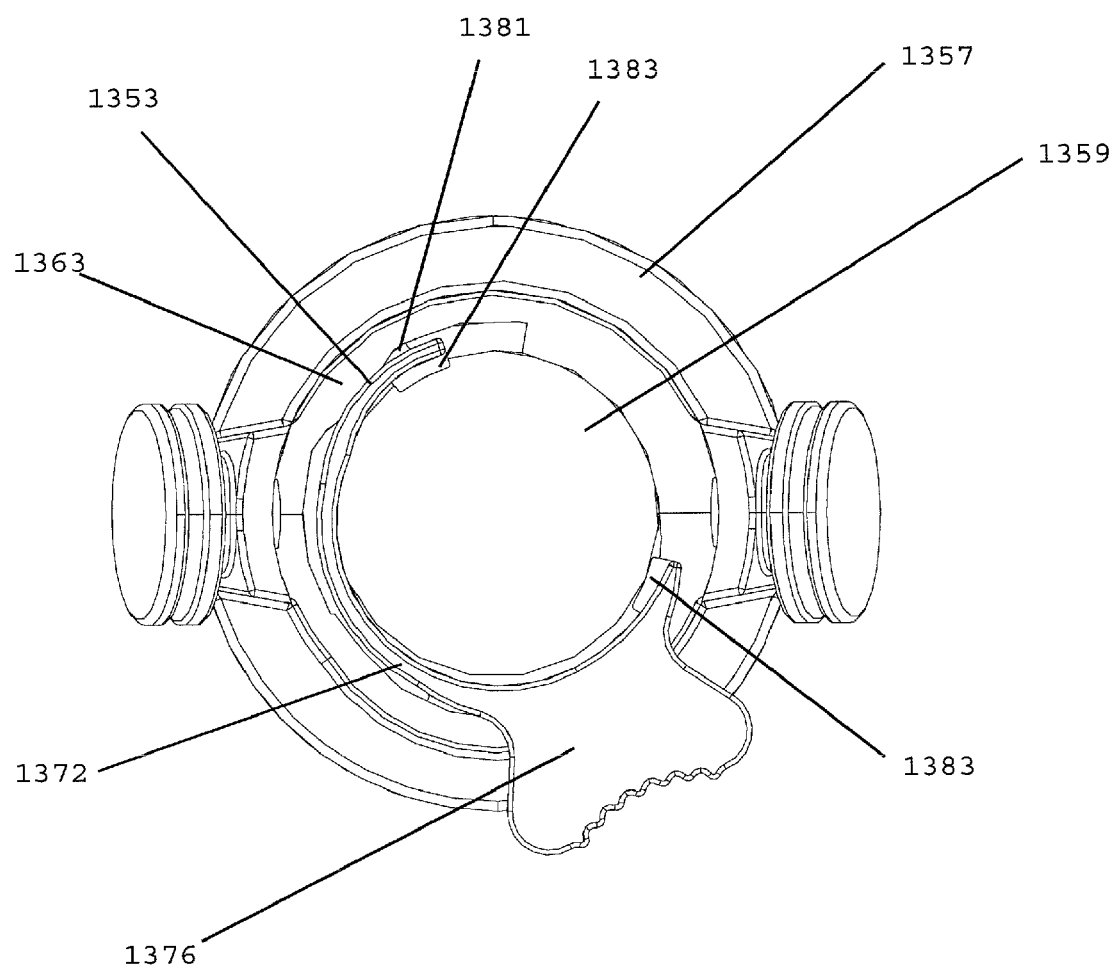
FIG. 19C is a top view of a base and the cannula retention member of the stability assembly of FIG. 19A.

With reference to FIGS. 18-19, embodiments of stability assembly are illustrated that are adapted for use with threaded or ribbed cannulae. FIG. 18A illustrates an exploded perspective view of a stability assembly for use with a ribbed cannula, FIG. 18B illustrates a perspective view of a cannula retention member of the stability assembly of FIG. 18A, and FIG. 18C illustrates a top view of a base and cannula retention member of the stability assembly of FIG. 18A. FIG. 19A illustrates an exploded perspective view of a stability assembly for use with a threaded cannula, FIG. 19B illustrates a perspective view of a cannula retention member of the stability assembly of FIG. 19A, and FIG. 19C illustrates a top view of a base and cannula retention member of the stability assembly of FIG. 19A.

With reference to FIG. 18 (including FIGS. 18A-18C), similar to the embodiment of FIGS. 1-6, in the embodiment illustrated in FIG. 18, the stability assembly comprises a stability member 1220 having a lumen therethrough 1222, a base 1257 comprising a passage 1259 defining an inner surface thereof, and a cannula retention member 1253. The base 1257 comprises a constriction, which can be formed by an increased wall thickness portion 1263 forming a ramped inner wall. As illustrated, the cannula retention member 1253 comprises an annular loop portion 1272 and an actuation lever 1276. At least one retention tab 1281 is formed on an outer surface of the annular loop portion 1272 to be positioned within a corresponding at least one retention slot 1265 in the base 1257. This tab-in-slot assembly can maintain a longitudinal position of the cannula retention member 1253 with respect to the base 1257 and can define a range of rotation of the cannula retention member 1253 relative to the base 1257 about the central longitudinal axis.

With continued reference to FIG. 18, at least one cannula retention tab 1283 is formed on an inner surface of the annular loop portion 1272. The cannula retention tab 1283 can be sized and configured to interface with one of a plurality of ribs 1212 on the ribbed cannula 1210. In the illustrated embodiment, two cannula retention tabs 1283 (FIGS. 18B, 18C) are formed on an inner surface of the annular loop portion 1272 and are longitudinally spaced apart with respect to the central longitudinal axis of the stability assembly. This spacing can allow each of the cannula retention tabs 1283 to interface with a different one of the ribs 1212 on the ribbed cannula 1210. In some embodiments, the cannula retention tabs 1283 can be at an approximately same longitudinal position to interface with a single one of the cannula retention tabs. In other embodiments, the cannula retention member 1253 can have more or fewer than two cannula retention tabs 1283.

In operation, as the cannula retention member 1253 is advanced from a first position in which a ribbed cannula 1210 can be inserted or moved within the passage 1259 to a second position in which the cannula is retained by the passage 1259, the cannula retention tabs 1283 on the cannula retention member 1253 are advanced radially inward within the passage 1259 such that when the cannula retention member 1253 is in a second position, the cannula retention tabs 1283 are seated between adjacent ribs 1212 of the ribbed cannula 1210. This seating of the cannula retention tabs 1283 interferes with the longitudinal movement of the ribs 1212 within the passage 1259, preventing longitudinal movement of the cannula. It is contemplated that any of the latch mechanisms described herein can be used to maintain the cannula retention member 1253 in the second position.

With reference to FIG. 19 (including FIGS. 19A-19C), similar to the embodiment of FIGS. 1-6, in the embodiment illustrated in FIG. 19, the stability assembly comprises a stability member 1320 having a lumen therethrough 1322, a base 1357 comprising a passage 1359 defining an inner surface thereof, and a cannula retention member 1353. The base 1357 comprises a constriction, which can be formed by an increased wall thickness portion 1363 forming a ramped inner wall. As illustrated, the cannula retention member 1353 comprises an annular loop portion 1372 and an actuation lever 1376. At least one retention tab 1381 is formed on an outer surface of the annular loop portion 1372 to be positioned within a corresponding at least one retention slot 1365 in the base 1357. This tab-in-slot assembly can maintain a longitudinal position of the cannula retention member 1353 with respect to the base 1357 and can define a range of rotation of the cannula retention member 1353 relative to the base 1357 about the central longitudinal axis.

With continued reference to FIG. 19, at least one cannula retention tab 1383 is formed on an inner surface of the annular loop portion 1372. The cannula retention tab 1383 can be sized and configured to interface with a helical thread 1312 on the threaded cannula 1310. In the illustrated embodiment, two cannula retention tabs 1383 (FIGS. 19B, 19C) are formed on an inner surface of the annular loop portion 1372 and are longitudinally spaced apart with respect to the central longitudinal axis of the stability assembly. In other embodiments, the cannula retention member 1353 can have more or fewer than two cannula retention tabs 1383.

In operation, as the cannula retention member 1353 is advanced from a first position in which a threaded cannula 1310 can be inserted or moved within the passage 1359 to a second position in which the cannula is retained by the passage 1359, the cannula retention tabs 1383 on the cannula retention member 1353 are advanced radially inward within the passage 1359 such that when the cannula retention member 1353 is in a second position, the cannula retention tabs 1383 are seated between adjacent helical coils of the helical thread 1312 of the threaded cannula 1310. This seating of the cannula retention tabs 1383 interferes with the longitudinal movement of the helical thread 1312 within the passage 1359, preventing longitudinal movement of the cannula 1310. It is contemplated that any of the latch mechanisms described herein can be used to maintain the cannula retention member 1353 in the second position.

Cam Pin Stability Assembly

Figure 20A:
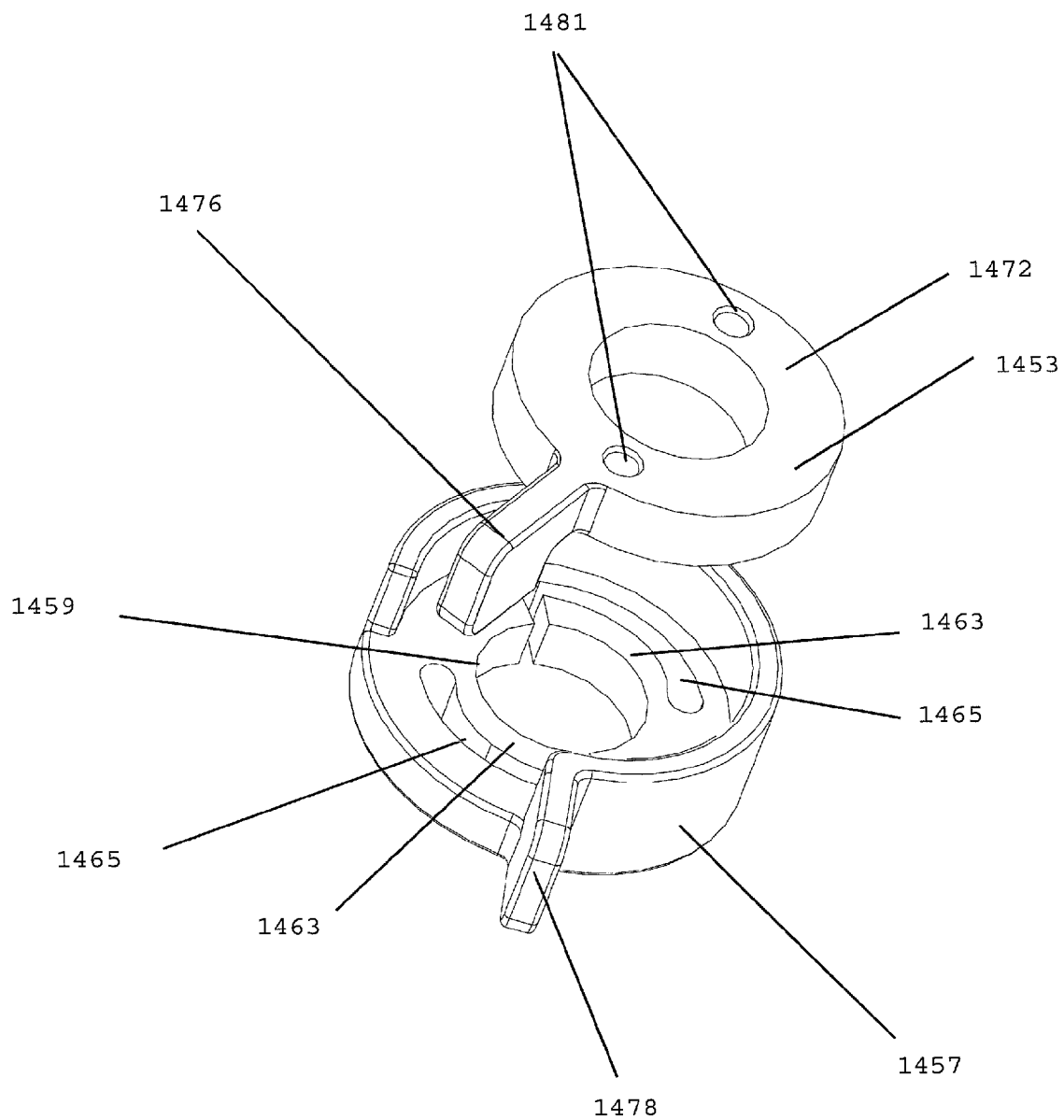
FIG. 20A is an exploded perspective view of a base and retention member of another embodiment of stability assembly.
Figure 20B:
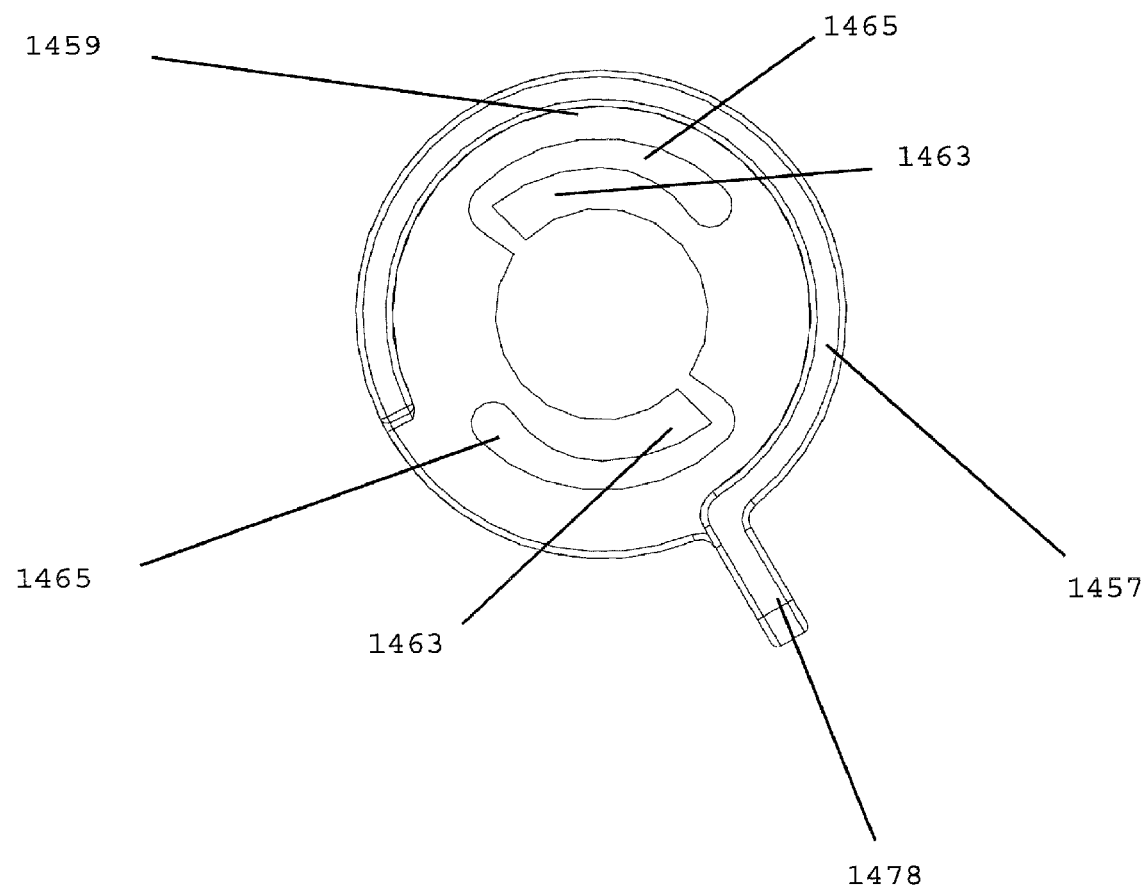
FIG. 20B is a top view of a base of the stability assembly of FIG. 20A.
Figure 20C:
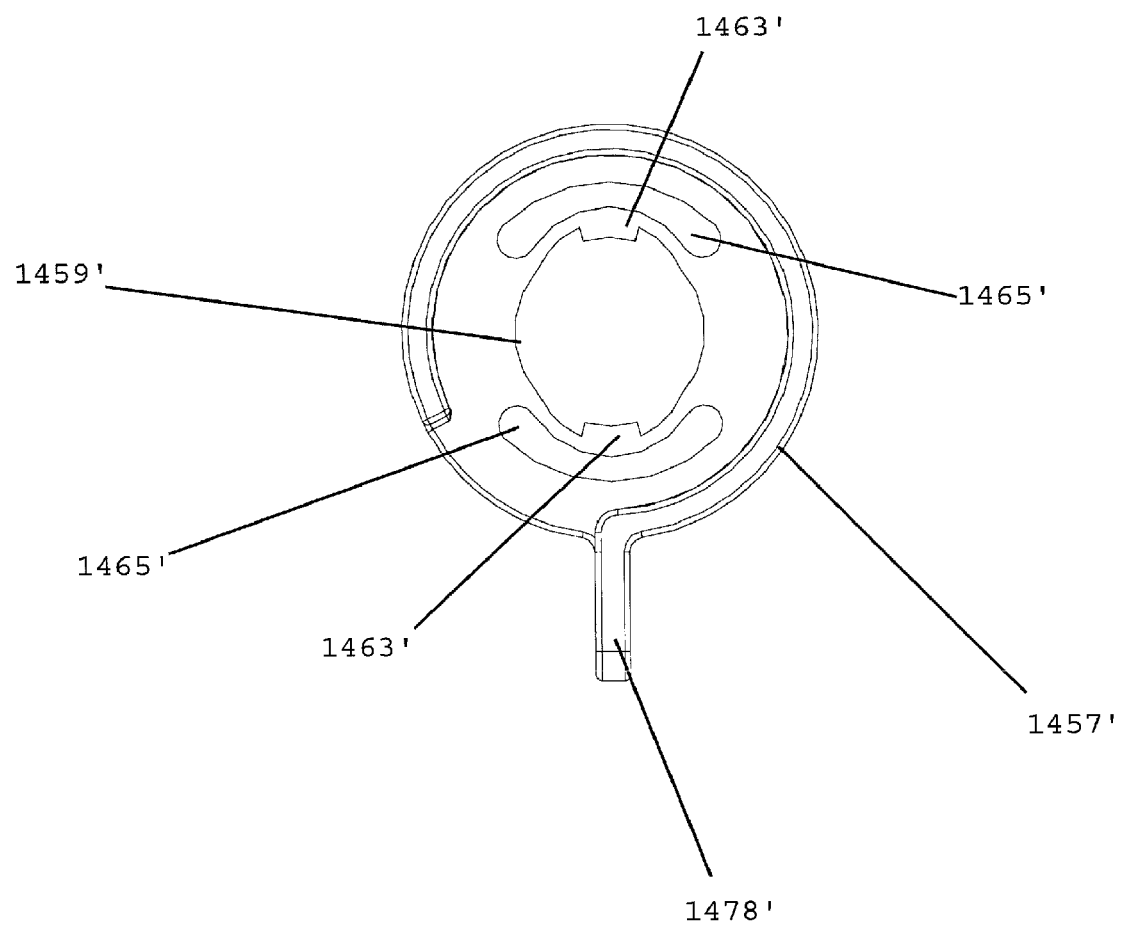
FIG. 20C is a top view of another embodiment of base for the stability assembly of FIG. 20A.

FIGS. 20A-20C illustrate another embodiment of stability assembly incorporating a cam pin mechanism to retain a cannula within the passage. Similar to the embodiment of FIGS. 1-6, in the embodiment illustrated in FIG. 20 (including FIGS. 20A-20C), the stability assembly comprises a base 1457 comprising a passage 1459 defining an inner surface thereof, and a cannula retention member 1453. The base 1457 can be configured to couple with a stability member as described herein with respect to other embodiments of stability assembly. The base 1457 comprises one or more flexible members 1463 positioned therein and at least partially defining a surface of the passage 1459. As illustrated, two flexible members 1463 are formed with slots 1465 adjacent thereto. The slots 1465 can have a variable profile such that movement of a pin within the slot in a certain direction can have a camming effect on the flexible members 1463, advancing them radially inwardly. This radial advancement of the flexible members 1463 can reduce an inner diameter of the passage 1459 to restrict motion of a cannula therein. The base 1457 can further comprise a base lever 1478.

With continued reference to FIG. 20, as illustrated, the cannula retention member 1453 comprises an annular ring portion 1472 and an actuation lever 1476. At least one pin 1481 protrudes from a surface of the annular ring portion 1472 to be positioned within a corresponding at least one retention slot 1465 in the base 1457.

In operation, a user can compress the base lever 1478 and the actuation lever 1476 towards one another to rotate the cannula retention member 1453 relative to the base 1457 about a central longitudinal axis of the stability assembly. As the cannula retention member 1453 is rotated about a central longitudinal axis of the stability assembly from a first position in which a cannula can be inserted or moved within the passage 1459 to a second position in which the cannula is retained by the passage 1459, the pins 1481 on the cannula retention member 1453 are advanced within the slots 1465 of the base 1457. This advancement of the pins 1465 in the slots causes the flexible members 1463 to advance radially inward. When the cannula retention member 1453 is in a second position, the inner diameter of the passage 1459 has been reduced such that longitudinal movement of a cannula in the passage 1459 is restricted.

In some embodiments, the wedge-like camming forces generated by the pin 1481 in slot 1465 motion can retain the cannula retention member 1453 in the second position. In other embodiments, a variable profile of the slots 1465 can be configured with a cam profile and a small relief or detent to retain the pins 1481 once the cannula retention member 1453 is in the second position, allowing the interaction of the pins and the slots to effectively maintain the cannula retention member 1453 in the second position. In other embodiments, it is contemplated that a latch mechanism such as one of the mechanisms described herein can be used to maintain the cannula retention member 1453 in the second position.

With reference to FIG. 20C, another embodiment of base 1457' for use with a cam pin stability assembly, such as that of FIGS. 20A-20B is illustrated. In the illustrated embodiment, the base 1457' can be configured to couple with a stability member as described herein with respect to other embodiments of stability assembly. The base 1457' comprises one or more flexible members 1463' positioned therein and at least partially defining a surface of the passage 1459'. The flexible members 1463' can comprise relatively thick cannula interface pads having a first and second relatively thin flexible rib extending from opposite ends thereof. As illustrated, two flexible members 1463' are formed with closed slots 1465' adjacent thereto. The slots 1465' can have a variable profile such that movement of a pin within the slot in a certain direction can have a camming effect on the flexible members 1463', advancing them radially inwardly. This radial advancement of the flexible members 1463' can reduce an inner diameter of the passage 1459' to restrict motion of a cannula therein. The base 1457' can further comprise a base lever 1478'.

Retention Loop Stability Assemblies

Figure 21A:
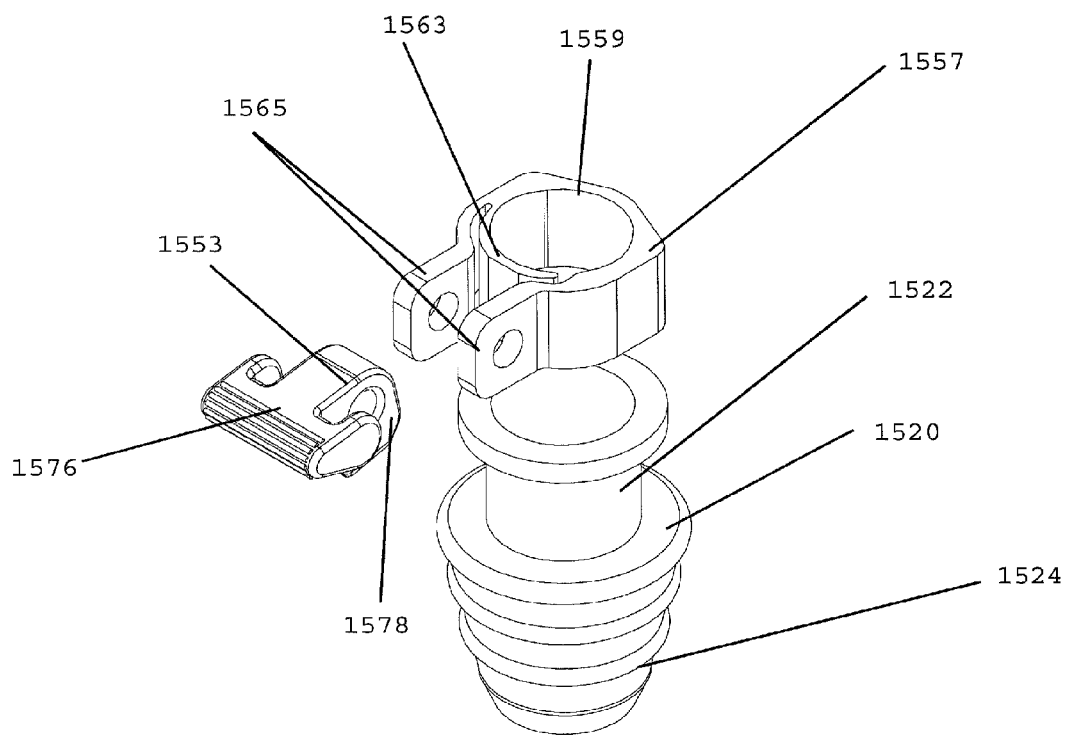
FIG. 21A is an exploded perspective view of another embodiment of stability assembly.
Figure 21B:
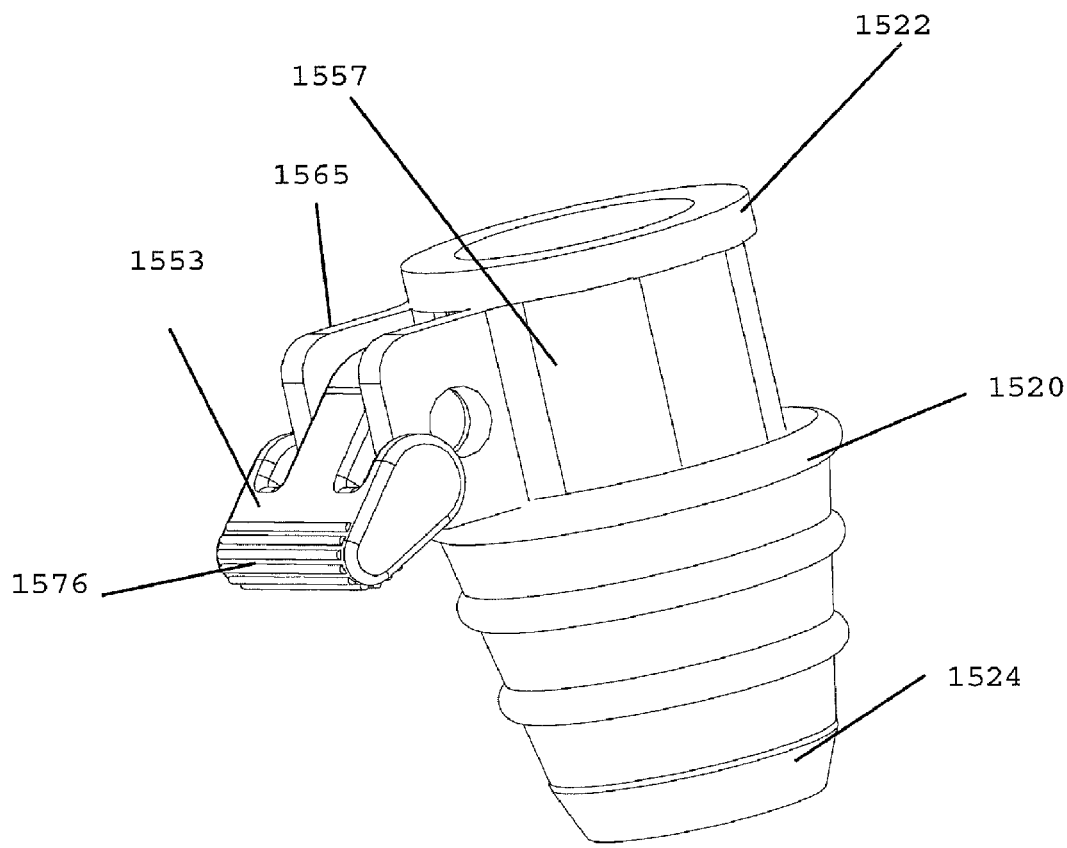
FIG. 21B is a perspective view of the stability assembly of FIG. 21A.
Figure 22A:
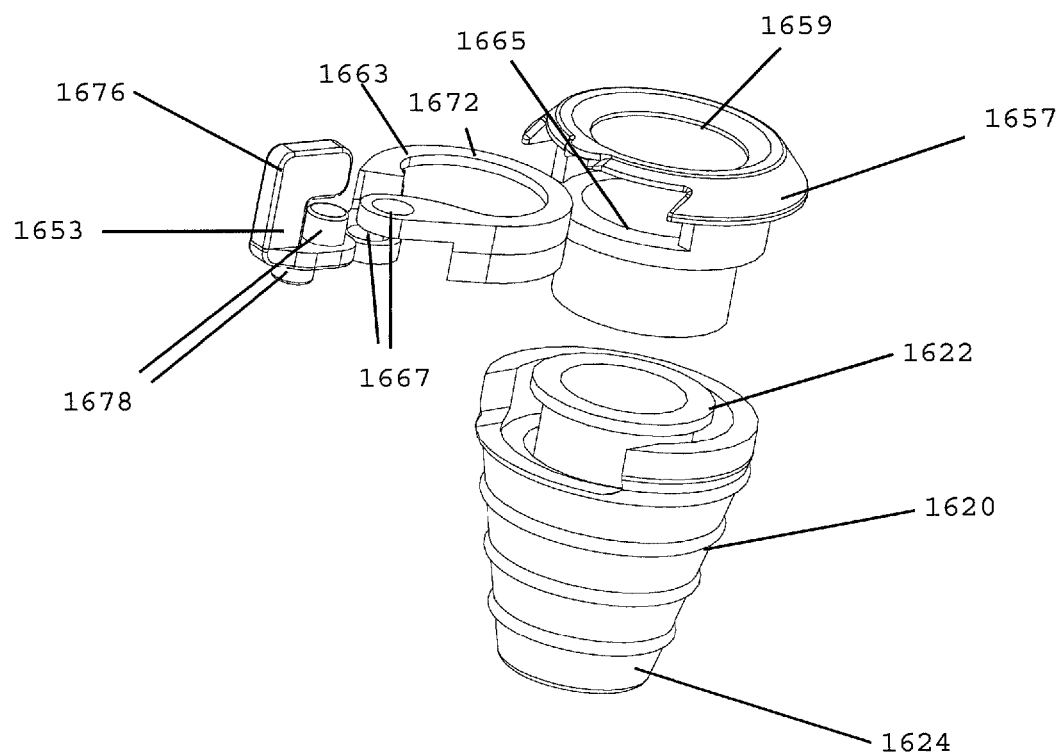
FIG. 22A is an exploded perspective view of another embodiment of stability assembly.
Figure 22B:
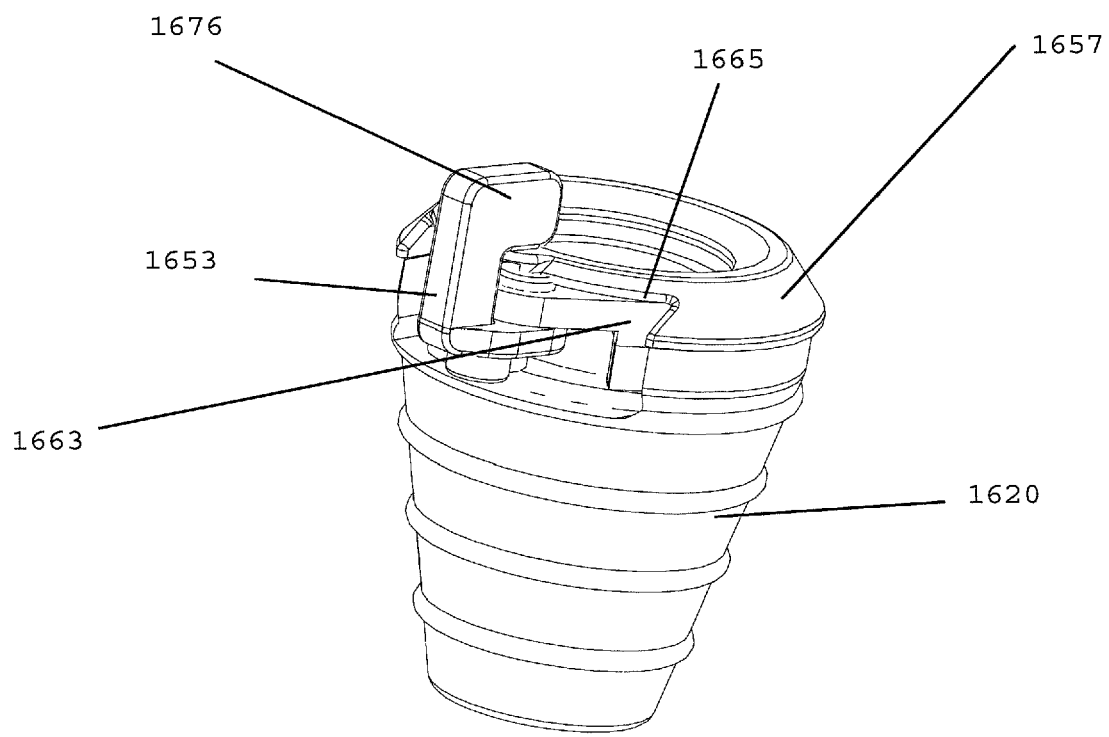
FIG. 22B is a perspective view of the stability assembly of FIG. 22A.

FIGS. 21-22 illustrate another embodiment of stability assembly incorporating a retention loop mechanism to retain a cannula within the passage. FIG. 21A illustrates an exploded perspective view of an embodiment of stability assembly having a retention loop mechanism. FIG. 21B illustrates a perspective view of the stability assembly of FIG. 21A. FIG. 22A illustrates an exploded perspective view of another embodiment of stability assembly having a retention loop mechanism. FIG. 22B illustrates a perspective view of the stability assembly of FIG. 22A.

With reference to FIG. 21 (including FIGS. 21A-21B), similar to the embodiment of FIGS. 1-6, in the illustrated embodiment, the stability assembly comprises a stability member 1520 and a base 1557 comprising a passage 1559 defining an inner surface thereof. The stability member 1520 comprises a proximal end 1522 having a reduced outer diameter, and a distal end 1524 contoured to be inserted into an entry port incision. The base 1559 includes a retention loop such as a flexible arm 1563 integrally formed therewith, which at least partially defines an inner diameter of the base.

With continued reference to FIG. 21, when assembled, in the illustrated embodiment, the base 1557 extends around a proximal portion 1522 of the stability member 1520, such that the stability member 1520 extends through the passage 1559 and the flexible arm 1563 contacts the stability member 1520. The stability assembly also comprises an actuator 1553 coupled to the base and configured to actuate the retention loop. In the illustrated embodiment, the actuator 1553 comprises an actuation lever 1576 at one end thereof, and a cam surface 1578 at an opposite end thereof. The cam surface 1578 bears on the flexible arm 1563.

In operation, the actuator 1553 is movable between a first position in which the inner diameter of the base has a first diameter and a second position in which the inner diameter of the base has a second diameter smaller than the first diameter. In the illustrated embodiment, the actuator 1553 is pivotably coupled to the base 1557 at a pair of mounting flanges 1565, and pivoting of the actuator 1553 advances the flexible arm 1563 radially inward by advancing the cam surface 1578 along the flexible arm 1563. This radial advancement of the flexible arm 1563 reduces the inner diameter of the passage 1559 to restrict motion of a cannula. To release the cannula or reposition the stability assembly along the cannula, a user can pivot the actuator 1553 in an opposite direction such that the diameter of the passage is increased.

In some embodiments, the cam profile can be shaped such that once pivoted to the second position, the actuator 1553 is maintained in the second position by camming forces. In other embodiments, a latch mechanism such as a ratchet or another mechanism described herein with respect to other embodiments of stability assembly can be used to maintain the actuator 1553 in the second position.

With reference to FIG. 22 (including FIGS. 22A-22B), similar to the embodiment of FIGS. 1-6, in the illustrated embodiment, the stability assembly comprises a stability member 1620 and a base 1657 comprising a passage 1659 defining an inner surface thereof. The stability member 1620 comprises a proximal end 1622 having a reduced outer diameter and configured to engage the base 1657, and a distal end 1624 contoured to be inserted into an entry port incision.

With continued reference to FIG. 22, the stability assembly comprises a retention assembly comprising the base 1657, a retention loop 1663, and an actuator 1653. The base 1657 comprises a slot 1665 formed therein and sized and configured to receive a portion of the retention loop 1663 therein. The retention loop 1663 comprises a loop portion 1672 and a connector portion configured to couple to the actuator 1653. In the illustrated embodiment, the connector portion comprises a plurality of apertures 1667 formed in a flanged surface of the retention loop 1663.

With continued reference to FIG. 22, when assembled, in the illustrated embodiment, the base 1657 extends around a proximal portion 1622 of the stability member 1620, such that the stability member 1620 extends through the passage 1659. The loop portion 1672 has a first portion extending around a portion of the base 1657 and a second portion extending through the slot 1665 of the base 1657 such that an inner diameter of the retention assembly is defined by an inner surface of the passage 1659 of the base 1657 and the second portion of the loop portion 1672. The actuator 1653 is coupled to the retention loop 1663 and configured to actuate the retention loop 1663. As illustrated, the actuator 1653 comprises an actuation lever 1676 at one end thereof, and a plurality of offset posts 1678 at an opposite end thereof.

In operation, the actuator 1653 is movable between a first position in which the inner diameter of the retention assembly has a first diameter and a second position in which the inner diameter of the retention assembly has a second diameter smaller than the first diameter. In the illustrated embodiment, the actuator 1653 is pivotably coupled to the retention loop 1663 by the pivot connection of the posts 1678 of the actuator 1653 at a pair of apertures 1667 of the retention loop 1663. In other embodiments, other pivot connections are contemplated to be within the scope of the present subject matter. In the illustrated embodiment, pivoting of the actuator 1653 reduces an inner diameter of the loop portion 1672. This diametric reduction reduces the inner diameter of the passage 1659 to restrict motion of a cannula. To release the cannula or reposition the stability assembly along the cannula, a user can pivot the base an opposite direction such that the diameter of the passage is increased.

In some embodiments, the connection between the actuator 1653 and the retention loop 1663 can be configured such that once the actuator 1653 is pivoted to the second position, the actuator 1653 is maintained in the second position. In other embodiments, a latch mechanism such as a ratchet or another mechanism discussed herein with respect to other embodiments of stability assembly can be used to maintain the actuator 1653 in the second position.

Stability Members

Figure 23A:
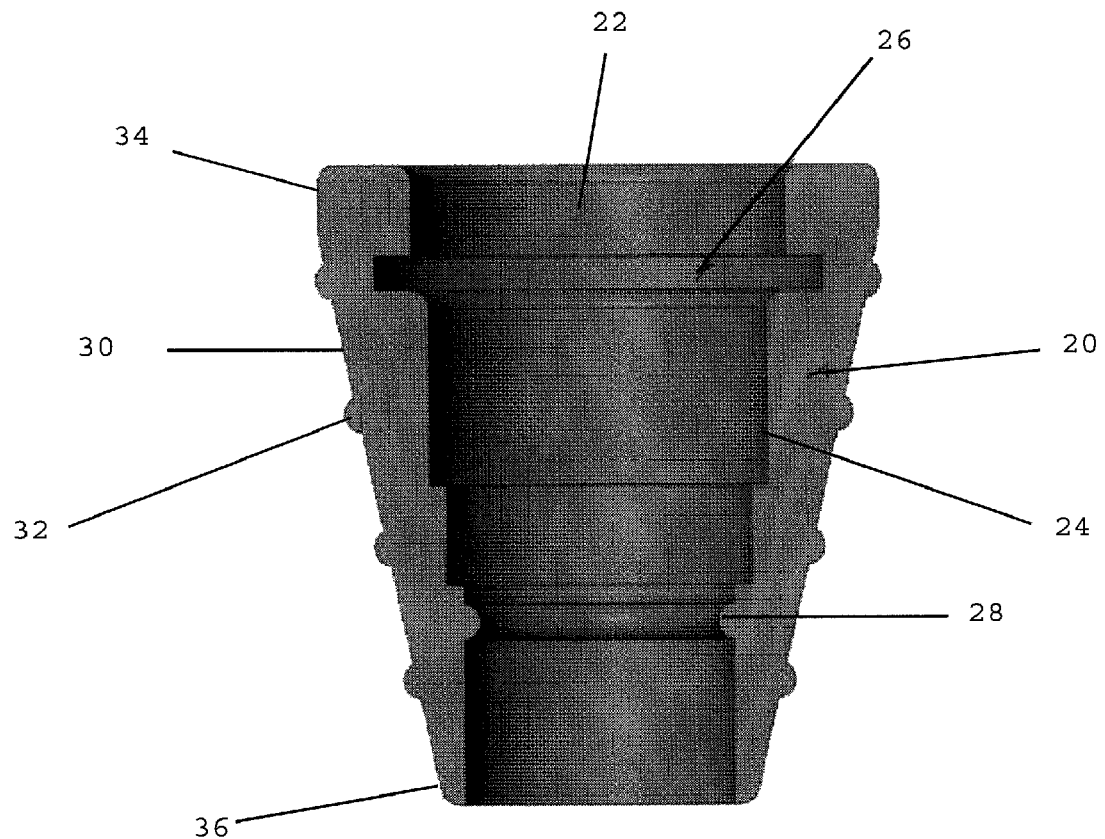
FIG. 23A is a longitudinal cross-sectional view of a stability member of a stability assembly.
Figure 23B:
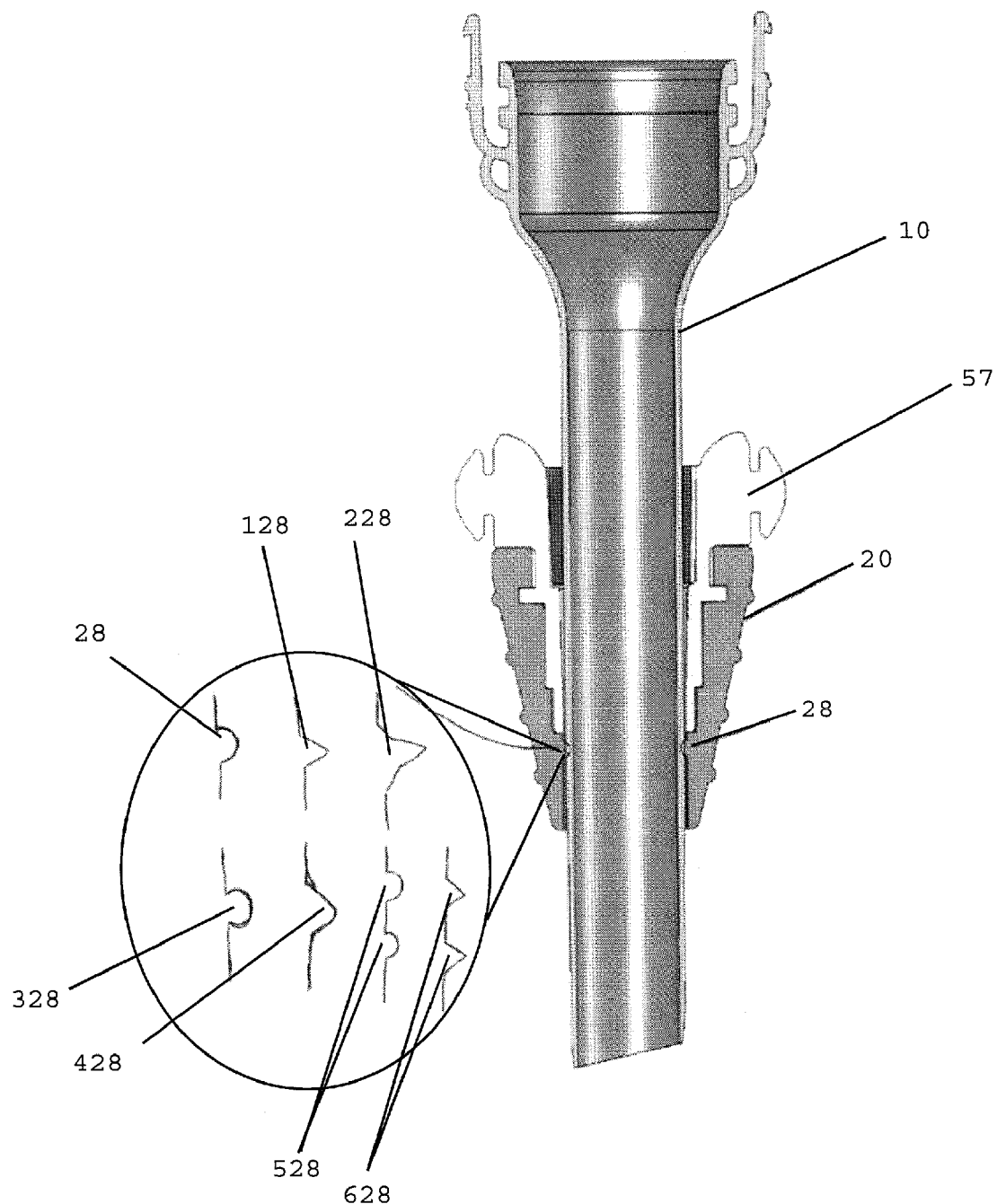
FIG. 23B is a longitudinal cross-sectional view of the stability member of FIG. 23A positioned about a cannula.
Figure 24A:
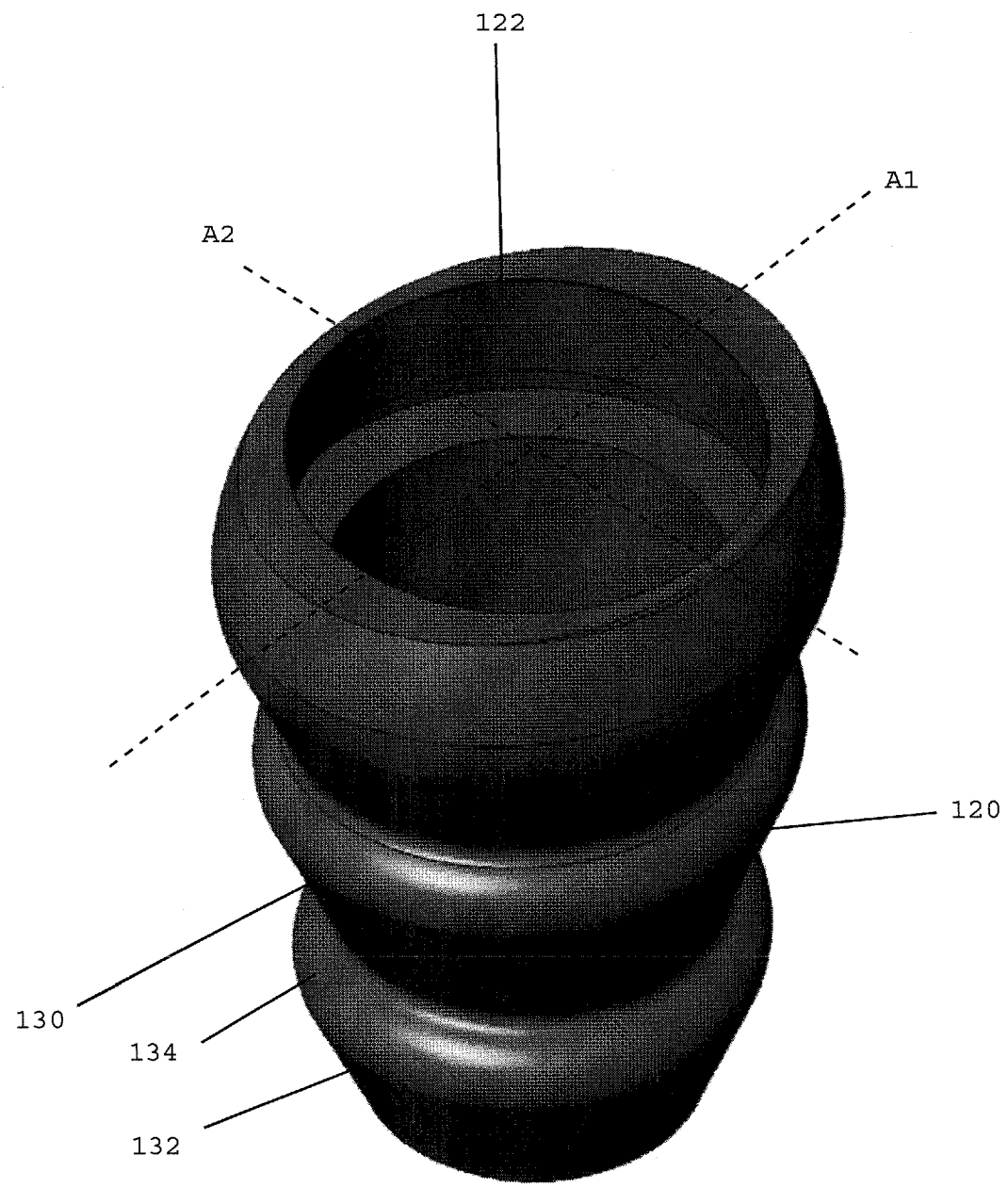
FIG. 24A is a perspective view of another embodiment of stability member.
Figure 24B:
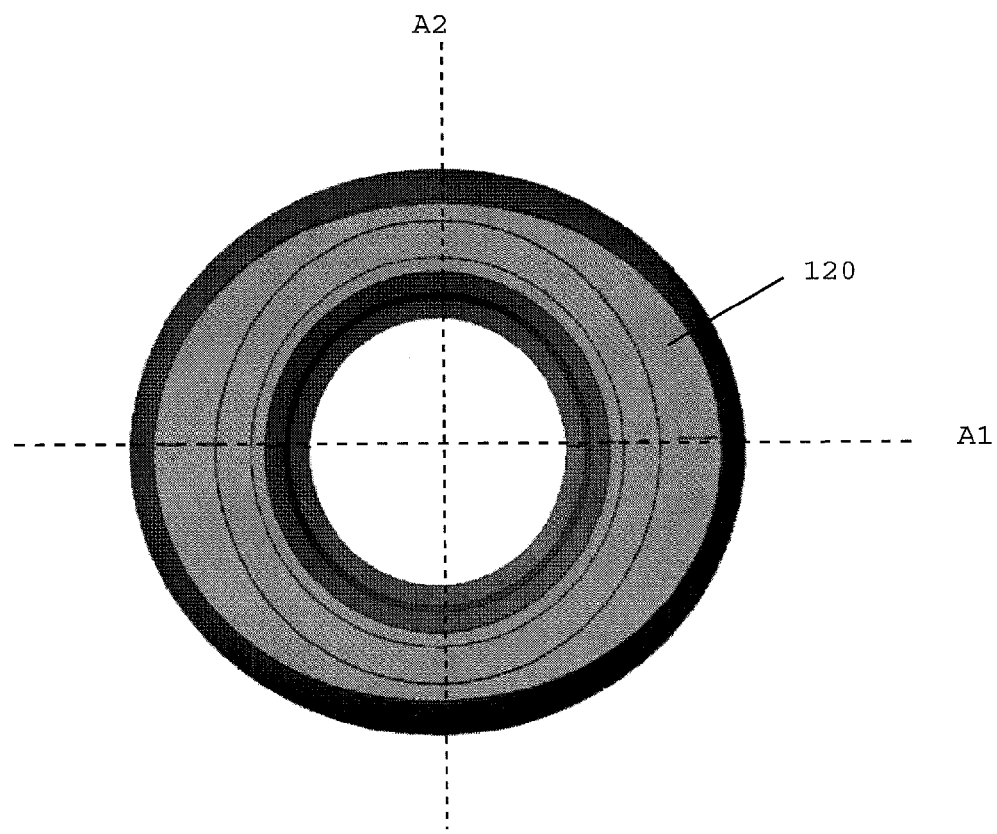
FIG. 24B is a top view of the stability member of FIG. 24A.

FIGS. 23-24 illustrate various embodiments of stability members that can be incorporated in a stability assembly, such as any of the stability assemblies described herein. FIG. 23A illustrates a longitudinal cross-sectional view of an embodiment of stability member. FIG. 23B illustrates a longitudinal cross-sectional view of the stability member of FIG. 23A having various embodiments of cannula seal in an exemplary embodiment stability assembly positioned on a cannula. FIG. 24A illustrates a perspective view of another embodiment of stability member having an elliptical profile. FIG. 24B illustrates a top view of the stability member of FIG. 24A.

With reference to FIG. 23 (which includes FIGS. 23A and 23B), a stability member 20 comprises a lumen 22 extending therethrough along a central longitudinal axis, an inner profile 24, and an outer profile 30. As discussed above with respect to FIGS. 1-6, the stability member 20 can be formed of a flexible material such as a silicone material.

In the illustrated embodiment, the inner profile 24 can be adapted to receive a portion of a base of a stability assembly. While the illustrated embodiment depicts one base 57 in the stability assembly, it is contemplated that the stability member 20 embodiments of FIG. 23 can form part of any of the embodiments of stability assembly described herein. The inner profile 24 can include an annular groove 26 formed therein configured to receive a flange protruding from a base. The inner profile 24 can also include segments having different inner diameters adapted to envelop segments of a base having different outer diameters. The inner profile can also include a cannula seal 28 such as a rounded annular protrusion. With reference to FIG. 23B, various profiles of cannula seal 28, 128, 228, 328, 428, 528, 628 can be used to seal the stability member 28 against an outer surface of a cannula 10, including protrusions having various curvilinear and angular geometries, and, in some embodiments, parallel sets of protrusions 528, 628 offering redundant seals. Desirably, the cannula seal profiles allow the cannula to be easily inserted or repositioned, while maintaining a fluid-tight seal between the cannula and the stability member.

In the illustrated embodiment, the outer profile 30 can adapted to seal with an entry port incision. In the illustrated embodiment, the stability member 20 has a generally conical shape tapering from a relatively large proximal end 34 to a relatively small distal end 36. The outer profile 30 of the stability member 20 can also include at least one retention feature 32 such as a ridge, protrusion, or ramped surface protruding therefrom. In the illustrated embodiment, the outer profile 30 includes a plurality of rounded annular ridges protruding therefrom. These ridges can aid in maintaining the stability member 20 in the incision site once inserted.

With reference to FIG. 24 (which includes FIGS. 24A-24B), in some embodiments, a stability member 120 for use with a stability assembly such as any of the stability assemblies described herein can have an eccentric profile such as a generally oblong or oval profile. The stability member 120 can have a generally cylindrical lumen 122 therethrough including an inner profile as discussed above with respect to FIG. 23 to receive a base of a stability assembly such as any of the embodiments of stability assembly discussed herein. However, an outer profile 130 of the stability member 120 can be eccentric, having a greater length along a first axis A1 than a second, orthogonal axis A2. In some embodiments, a base of a stability assembly can be rotatable within the lumen 122 with respect to the stability member 120 such that the base can be positioned as desired with respect to the oblong dimensions of the stability member 120. Advantageously, since an entry incision is typically a linear cut, an oval or oblong profile can often conform better to the incision during placement and use.

With continued reference to FIG. 24, the outer profile 130 of the stability member 120 can be contoured to increase sealing and securing of the cone with the incision. In the illustrated embodiment, the other profile 130 includes a plurality of ramp surfaces 132 alternating with rounded detents to facilitate insertion of the stability member 120 and its maintenance in the incision. In other embodiments, it is contemplated that an oblong stability member can include other retention members such as rounded annular ridges as discussed above with respect to FIG. 23.

Although the present invention has been described in certain specific aspects, many additional modifications and variations would be apparent to those skilled in the art. For example, it is contemplated that various combinations of stability member and latch mechanism could be made to provide different seals/profiles for particular entries and/or incision sites. It is therefore to be understood that the present inventions may be practiced otherwise than specifically described, including various changes in the size, shape and materials, without departing from the scope and spirit of the present application. Thus, embodiments of the present application should be considered in all respects as illustrative and not restrictive. The scope of the present application should therefore be determined only by a fair reading of the claims which follow.

What is claimed is:

1. A stability assembly for a trocar system comprising:
   a stability member adapted to seal an entry port incision, the stability member having a lumen extending therethrough, the lumen defining a longitudinal axis of the stability assembly and the stability member having a conical profile about the longitudinal axis;
   a base positioned at least partially within the lumen, the base having a passage extending along the longitudinal axis, the passage adapted to receive a cannula therein; and
   a retention member positioned such that the retention member and the passage define an inner diameter of the stability assembly; and
   wherein the retention member is rotatable about the longitudinal axis between a first position wherein the stability assembly has a first inner diameter and a second position wherein the stability assembly has a second inner diameter smaller than the first inner diameter and wherein the retention member is unbiased towards either one of the first position and the second position and is actively engageable such that the retention member in the first position remains in the first position and the retention member in the second position remains in the second position.

2. The stability assembly of claim 1, wherein the base comprises a slot formed therein and the retention member comprises a tab formed thereon, the tab positioned in the slot to maintain a position of the retention member with respect to the base along the longitudinal axis.

3. The stability assembly of claim 1, wherein the retention member comprises at least one protrusion formed on an inner surface thereof.

4. The stability assembly of claim 3, wherein the at least one protrusion comprises a plurality of protrusions, each of the protrusions at a same longitudinal position with respect to the longitudinal axis.

5. The stability assembly of claim 3, wherein the at least one protrusion comprises a plurality of protrusions spaced apart from one another with respect to the longitudinal axis.

6. The stability assembly of claim 1, wherein the passage of the base comprises a ramped inner surface positioned such that the retention member is advanced over the ramped inner surface during movement of the retention member from the first position to the second position.

7. The stability assembly of claim 1, wherein the stability member is contoured to facilitate insertion to the entry port incision.

8. The stability assembly of claim 7, wherein the stability member has an oblong profile about a lateral axis substantially perpendicular to the longitudinal axis.

9. The stability assembly of claim 8, wherein the base is rotatable about the longitudinal axis with respect to the stability member.

10. The stability assembly of claim 7, wherein the stability member is contoured to resist removal from the entry port incision.

11. The stability assembly of claim 7, wherein the base comprises a central opening forming the passage and at least one slot formed adjacent the passage and spaced from the passage by a rib, and wherein the retention member comprises a protrusion positioned in the slot and configured to advance the rib towards the passage as the retention member is rotated from the first position to the second position.

12. The stability assembly of claim 1, wherein the retention member comprises:
    a retention loop having a first portion extending around a portion of the base; and
    an actuator coupled to the retention loop and configured to actuate the retention loop, wherein rotation of the retention member about the longitudinal axis between the first position and the second position comprises rotation of the actuator about the longitudinal axis between the first position and the second position.

13. The stability assembly of claim 1, wherein the retention member comprises:
    a retention loop having a first portion extending around a portion of the base; and
    an actuator coupled to the retention loop and configured to actuate the retention loop, wherein rotation of the retention member about the longitudinal axis between the first position and the second position comprises rotation of the actuator with respect to the retention loop between the first position and the second position.

14. The stability assembly of claim 1, wherein the lumen of the stability member comprises an annular groove formed therein configured to receive a portion of the base.

15. The stability assembly of claim 1, wherein the lumen of the stability member comprises a cannula seal.

16. The stability assembly of claim 15, wherein the cannula seal comprises an annular protrusion.

17. The stability assembly of claim 14, wherein the base comprises a flange protruding radially outwardly therefrom and wherein the annular groove is sized and configured to receive the flange of the base.

18. The stability assembly of claim 15, wherein the cannula seal is configured to maintain a fluid-tight seal with the cannula inserted through the passage of the base.

* * * * *